United States Patent
Berg et al.

(10) Patent No.: US 7,345,050 B2
(45) Date of Patent: *Mar. 18, 2008

(54) PYRIMIDINE COMPOUNDS

(75) Inventors: Stefan Berg, Södertälje (SE); Sven Hellberg, Södertälje (SE)

(73) Assignee: AstraZeneca AB, Sodertalje (SE)

( * ) Notice: Subject to any disclaimer, the term of this patent is extended or adjusted under 35 U.S.C. 154(b) by 464 days.

This patent is subject to a terminal disclaimer.

(21) Appl. No.: 10/468,604

(22) PCT Filed: Feb. 18, 2002

(86) PCT No.: PCT/SE02/00271

§ 371 (c)(1),
(2), (4) Date: Aug. 19, 2003

(87) PCT Pub. No.: WO02/065979

PCT Pub. Date: Aug. 29, 2002

(65) Prior Publication Data

US 2004/0077642 A1   Apr. 22, 2004

(30) Foreign Application Priority Data

Feb. 20, 2001   (SE) .................................. 0100569

(51) Int. Cl.
C07D 471/04 (2006.01)
C07D 401/14 (2006.01)
C07D 239/42 (2006.01)
C07D 235/02 (2006.01)
A61K 31/4188 (2006.01)
A61K 31/437 (2006.01)
A61K 31/506 (2006.01)
A61P 35/00 (2006.01)

(52) U.S. Cl. ............... 514/269; 514/272; 514/300; 544/321; 544/331; 546/121

(58) Field of Classification Search ........ 544/321, 544/331; 546/121; 514/269, 272, 300
See application file for complete search history.

(56) References Cited

U.S. PATENT DOCUMENTS

| 5,521,184 A | 5/1996 | Zimmermann | 514/252 |
| 5,958,935 A | 9/1999 | Davis et al. | 514/275 |
| 6,855,719 B1 * | 2/2005 | Thomas et al. | 514/269 |

FOREIGN PATENT DOCUMENTS

WO   0114375   3/2001

OTHER PUBLICATIONS

Patel et al. Biochem. Soc. Trans. 32(5), 803-808, 2004.*
Jope et al., Trends in Biochemical Sciences 29(2), 95-102, 2004.*
Imahori et al., J. Biochem. 121, 179-188 (1997).
Vijayaraghavan, et al., Biol. Reprod. 62/6, 1647-54 (2000).
Nikoulina, et al., Diabetes 49/2, 263-71 (2000).
Kozlovsky, et al., Am. J. Psychiatry 157/5, 831-3 (2000).
Gat, et al., Cell 95/5, 605-14 (1998).
Stambolic, et al., Curr. Biol. 6, 1664-1668 (1996).
Klein et al., PNAS 93, 8455-59 (1996).
Hoshi, et al., PNAS 93, 2719-2723 (1996).
Bhat, et al., PNAS 97, 11074-79 (2000).
Cotter, et al., NeuroReport 9, 1379-83 (1998).
STN International, File CAPLUS, CAPLUS, accession No. 1970:445054, Doc. No. 73:45054, Alberola, et al.
STN International, File CAPLUS, CAPLUS accession No. 1981:138783, Doc. No. 94:138783, Draney, et al.
STN International, File CAPLUS, CAPLUS accession No. 1967:99945, Doc. No. 66:99945, Borkman, et al.
STN International, File CAPLUS, CAPLUS accession No. 1998:527309, Doc. No. 129:148822, Ottosen, et al.
STN International, File CAPLUS, CAPLUS accession No. 1967:33262, Doc. No. 66:33262, Tsekhanskii, et al.
STN International, File CAPLUS, CAPLUS accession No. 1977: 139625, Doc. No. 86:139625, Robertson, et al.
STN International, File CAPLUS, CAPLUS accession No. 1974:413253, Doc. No. 81:13253, Fourneau, et al.
STN International, File CALOD, CALOD accession No. CA60:514a, Ermolaeva, et al.
STN International, File CAPLUS, CAPLUS accession No. 1981:515545, Doc. No. 95:115545, Karjanaynen, et al.
STN International, File CAPLUS, CAPLUS accession No. 1970:509404, Doc. No. 73:109404, Rybakova, et al.
STN International, File CAPLUS, CAPLUS accession No. 1967:516302, Doc. No. 67:116302, Nishida, S.

* cited by examiner

Primary Examiner—Venkataraman Balasubramanian

(57) ABSTRACT

The present invention relates to new compounds of the formula (I) a process for their preparation, pharmaceutical formulations containing said therapeutically active compounds and to the use of said active compounds in therapy, as well as intermediates used in the preparation of said active compounds

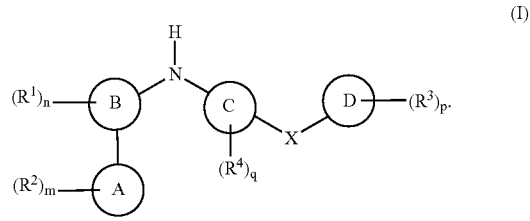

(I)

5 Claims, No Drawings

PYRIMIDINE COMPOUNDS

FIELD OF THE INVENTION

The present invention relates to new compounds of the formula I, as a free base or a pharmaceutically acceptable salt thereof, process for their preparation, pharmaceutical formulations containing said compounds and to the use of said active compounds in therapy.

An object of the invention is to provide compounds of formula I for therapeutic use, especially compounds that are useful for the treatment and/or prophylaxis of conditions associated with glycogen synthase kinase-3 (GSK3) in mammals including man. Particularly compounds of formula I exhibiting a selective affinity for GSK-3.

It is also an object of the invention to provide compounds with a therapeutic effect after oral administration.

BACKGROUND OF THE INVENTION

Glycogen synthase kinase 3 (GSK3) is a serine/threonine protein kinase composed of two isoforms ($\alpha$ and $\beta$), which are encoded by distinct genes but are highly homologous within the catalytic domain. GSK3 is highly expressed in the central and peripheral nervous system. GSK3 phosphorylates several substrates including tau, $\beta$-catenin, glycogen synthase, pyruvate dehydrogenase and elongation initiation factor 2b (eIF2b). Insulin and growth factors activate protein kinase B, which phosphorylates GSK3 on serine 9 residue and inactivates it.

Alzheimer's Disease (AD) Dementias, and Taupathies

AD is characterized by cognitive decline, cholinergic dysfunction and neuronal death, neurofibrillary tangles and senile plaques consisting of amyloid-$\beta$ deposits. The sequence of these events in AD is unclear, but believed to be related. Glycogen synthase kinase 3$\beta$ (GSK3$\beta$) or Tau ($\tau$) phosphorylating kinase selectively phosphorylates the microtubule associated protein $\tau$ in neurons at sites that are hyperphosphorylated in AD brains. Hyperphosphorylated protein $\tau$ has lower affinity for microtubules and accumulates as paired helical filaments, which is the main component that constitute neurofibrillary tangles and neuropil threads in AD brains. This results in depolymerization of microtubules, which leads to dying back of axons and neuritic dystrophy. Neurofibrillary tangles are consistently found in diseases such as AD, amyotrohic lateral sclerosis, parkinsonism-dementia of Gaum, corticobasal degeneration, dementia pugilistica and head trauma, Down's syndrome, postencephalatic parkinsoism, progressive supranuclear palsy, Niemann-Pick's Disease and Pick's Disease. Addition of amyloid-$\beta$ to primary hippocampal cultures results in hyperphosphorylation of $\tau$ and a paired helical filaments-like state via induction of GSK3$\beta$ activity, followed by disruption of axonal transport and neuronal death (Imahori and Uchida., J. Biochem 121:179-188, 1997). GSK3$\beta$ preferentially labels neurofibrillary tangles and has been shown to be active in pre-tangle neurons in AD brains. GSK3 protein levels are also increased by 50% in brain tissue from AD patients. Furthermore, GSK3$\beta$ phosphorylates pyruvate dehydrogenase, a key enzyme in the glycolytic pathway and prevents the conversion of pyruvate to acetyl-Co-A (Hoshi et al., PNAS 93:2719-2723, 1996). Acetyl-Co-A is critical for the synthesis of acetylcholine, a neurotransmitter with cognitive functions. Thus, GSK3$\beta$ inhibition may have beneficial effects in progression as well as the cognitive deficits associated with Alzheimer's disease and other above-referred to diseases.

Chronic and Acute Neurodegenerative Diseases

Growth factor mediated activation of the PI3K/Akt pathway has been shown to play a key role in neuronal survival. The activation of this pathway results in GSK3$\beta$ inhibition. Recent studies (Bhat et al., PNAS 97:11074-11079 (2000)) indicate that GSK3$\beta$ activity is increased in cellular and animal models of neurodegeneration such as cerebral ischemia or after growth factor deprivation. For example, the active site phosphorylation was increased in neurons vulnerable to apoptosis, a type of cell death commonly thought to occur in chronic and acute degenerative diseases such as Alzheimer's Disease, Parkinson's Disease, amyotrophic lateral sclerosis, Huntington's Disease and HIV dementia, ischemic stroke and head trauma. Lithium was neuroprotective in inhibiting apoptosis in cells and in the brain at doses that resulted in the inhibition of GSK3$\beta$. Thus GSK3$\beta$ inhibitors could be useful in attenuating the course of neurodegenerative diseases.

Bipolar Disorders (BD)

Bipolar Disorders are characterised by manic episodes and depressive episodes. Lithium has been used to treat BD based on its mood stabilising effects. The disadvantage of lithium is the narrow therapeutic window and the danger of overdosing that can lead to lithium intoxication. The recent discovery that lithium inhibits GSK3 at therapeutic concentrations has raised the possibility that this enzyme represents a key target of lithium's action in the brain (Stambolic et al., Curr. Biol. 6:1664-1668, 1996; Klein and Melton; PNAS 93:8455-8459, 1996). Inhibition of GSK3$\beta$ may therefore be of therapeutic relevance in the treatment of BD as well as in AD patients that have affective disorders.

Schizophrenia

GSK3 is involved in signal transduction cascades of multiple cellular processes, particularly during neural development. Kozlovsky et al (Am J Psychiatry 2000 May; 157(5):831-3) found that GSK3$\beta$ levels were 41% lower in the schizophrenic patients than in comparison subjects. This study indicates that schizophrenia involves neurodevelopmental pathology and that abnormal GSK3 regulation could play a role in schizophrenia. Furthermore, reduced $\beta$-catenin levels have been reported in patients exhibiting schizophrenia (Cotter et al., Neuroreport 9:1379-1383 (1998)).

Diabetes

Insulin stimulates glycogen synthesis in skeletal muscles via the dephosphorylation and thus activation of glycogen synthase via dephosphorylation. Under resting conditions, GSK3 phosphorylates and inactivates glycogen synthase. GSK3 is also over-expressed in muscles from Type II diabetic patients (Nikoulina et al., Diabetes 2000 February; 49(2):263-71). Inhibition of GSK3 increases the activity of glycogen synthase thereby decreasing glucose levels by its conversion to glycogen. GSK3 inhibition may therefore be of therapeutic relevance in the treatment of Type I and Type II diabetes and diabetic neuropathy.

Hair Loss

GSK3 phosphorylates and degrades $\beta$-catenin. $\beta$-catenin is an effector of the pathway for keratonin synthese. $\beta$-catenin stabilisation may be lead to increase hair development. Mice expressing a stabilised $\beta$-catenin by mutation of sites phosphorylated by GSK3 undergo a process resembling de novo hair morphogenesis (Gat et al., Cell Nov. 25, 1998;95 (5):605-14)). The new follicles formed sebaceous glands and dermal papilla, normally established only in embryogenesis. Thus GSK3 inhibition may offer treatment for baldness.

Oral Contraceptives

Vijajaraghavan et al. (Biol Reprod 2000 June; 62 (6): 1647-54) reported that GSK3 is high in motile versus immotile sperm. Immunocytochemistry revealed that GSK3 is present in the flagellum and the anterior portion of the sperm head. These data suggest that GSK3 could be a key element underlying motility initiation in the epididymis and regulation of mature sperm function. Inhibitors of GSK3 could be useful as contraceptives for males.

DISCLOSURE OF THE INVENTION

The object of the present invention is to provide compounds having a selective inhibiting effect at GSK3 as well as having a good bioavailability. The effect on other kinases chosen from, for example CDK2, has been investigated.

Accordingly, the present invention provides a compound of the formula I

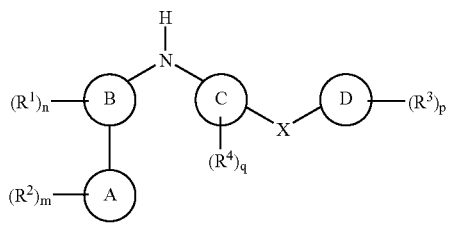

(I)

wherein:

X is $C_{0-6}$alkyl-U—$C_{0-6}$alkyl, $(C_{2-6}$alkenyl$)_{0-1}$-U—$(C_{2-6}$alkenyl$)_{0-1}$ or $(C_{2-6}$alkynyl$)_{0-1}$-U—$(C_{2-6}$alkyny$)_{0-1}$, wherein any $C_{1-6}$alkyl, $C_{2-6}$alkenyl, $C_{2-6}$alkynyl, where a $CH_2$ group can optionally be replaced by a CO group, and may be optionally substituted on a carbon by one or more G and each carbon may be replaced by a N, O, or S and wherein said nitrogen may be optionally substituted by a group Q;

U is CO or $C(OR^5)R^6$;

Ring A is imidazo[1,2a]pyrid-3-yl or pyrazolo[2,3a]pyrid-3-yl;

Ring B is a 5- or 6-membered heteroaromatic ring containing heteroatoms selected from N, O and S of which at least one atom is selected from nitrogen;

Ring C is a phenyl ring or a 5- or 6-membered heteroaromatic ring containing heteroatoms selected from N, O and S;

Ring D is a phenyl ring or a 5- or 6-membered heteroaromatic ring containing heteroatoms selected from N, O and S and said phenyl ring or 5- or 6-membered heteroaromatic ring may optionally be fused with a 5- or 6-membered saturated, partially saturated or unsaturated ring optionally containing atoms selected from C, N, O and S and wherein if said heterocyclic group contains an —NH— moiety that nitrogen may be optionally substituted by a group Q;

$R^1$ is hydrogen, halo, nitro, cyano, hydroxy, fluoromethyl, difluoromethyl, trifluoromethyl, fluoromethoxy, difluoromethoxy, trifluoromethoxy, $NH_2$, NHOH, NHCN, $(CO)C_{1-3}$alkyl, CH=$NOR^7$, (C=NH)$NR^7R^8$, $CONH_2$, SH, $SC_{1-3}$alkyl, $SO_2NH_2$, $SONH_2$, $C_{1-3}$alkyl, $C_{3-6}$cycloalkyl, $C_{2-3}$alkenyl, $C_{2-3}$alkynyl, $C_{1-3}$alkoxy, $O(CO)C_{1-3}$alkyl, $NHC_{1-3}$alkyl, $N(C_{1-2}$alkyl$)_2$, NH(CO)$C_{1-3}$alkyl, $CONHC_{1-3}$alkyl, $CON(C_{1-3}$alkyl$)_2$, $SOC_{1-3}$alkyl, $SO_2C_{1-3}$alkyl, $SO_2NH(C_{1-3}$alkyl), $SO_2N(C_{1-3}$alkyl$)_2$, $SONHC_{1-3}$alkyl, or $SON(C_{1-3}$alkyl$)_2$, wherein any $C_{1-2}$alkyl, $C_{1-3}$alkyl, $C_{2-3}$alkenyl or $C_{2-3}$alkynyl may be optionally substituted on any carbon atoms by one or more J;

n is 1, 2 or 3, wherein each $R^1$ above may be the same or different;

$R^2$, $R^3$ and $R^4$ are attached to a ring carbon and are independently selected from hydrogen, halo, nitro, CHO, $C_{0-6}$alkylCN, $OC_{0-6}$alkylCN, $C_{0-6}$alkyl$OR^7$, $OC_{1-6}$alkyl$OR^7$, fluoromethyl, difluoromethyl, trifluoromethyl, fluoromethoxy, difluoromethoxy, trifluoromethoxy, $C_{0-6}$alkyl$NR^7R^8$, $OC_{1-6}$alkyl$NR^7R^8$, $OC_{1-6}$alkyl$OC_{1-6}$alkyl$NR^7R^8$, NHOH, $NR^7OR^8$, NHCN, $(CO)C_{1-3}$alkyl, CH=$NOR^7$, (C=NH)$NR^7R^8$, $C_{0-6}$alkyl$CO_2R^7$, $OC_{1-6}$alkyl$CO_2R^7$, $C_{0-6}$alkyl$CONR^7R^8$, $OC_{1-6}$alkyl$CONR^7R^8$, $C_{0-6}$alkyl$NR^7(CO)R^7$, $O(CO)NR^7R^8$, $NR^9(CO)OR^7$, $NR^7(CO)NR^7R^8$, $O(CO)OR^7$, $O(CO)R^7$, $C_{0-6}$alkyl$COR^7$, $OC_{1-6}$alkyl$COR^7$, $NR^7(CO)(CO)R^7$, $NR^7(CO)(CO)NR^7R^8$, $SR^7$, $C_{0-6}$alkyl$(SO_2)NR^7R^8$, $OC_{1-6}$alkyl$NR^7(SO_2)R^8$, $OC_{1-6}$alkyl$(SO_2)NR^7R^8$, $C_{0-6}$alkyl$(SO)NR^7R^8$, $OC_{1-6}$alkyl$(SO)NR^7R^8$, $SO_3R^7$, $C_{0-6}$alkyl$NR^7(SO_2)NR^7R^8$, $C_{0-6}$alkyl$NR^7(SO)R^8$, $C_{0-6}$alkyl$SO_2R^7$, $C_{0-6}$alkyl$SOR^7$, $C_{1-6}$alkyl, $C_{2-6}$alkenyl, $C_{2-6}$alkynyl, $C_{0-6}$alkyl$C_{3-6}$cycloalkyl, $C_{0-6}$alkylaryl, $C_{0-6}$alkylheterocyclic group, wherein any $C_{1-6}$alkyl, $C_{2-6}$alkenyl, $C_{2-6}$alkynyl, $C_{0-6}$alkyl$C_{3-6}$cycloalkyl, $C_{0-6}$alkylaryl or $C_{0-6}$alkylheterocyclic group may be optionally substituted on carbon by one or more G; and wherein if said heterocyclic group contains an —NH— moiety that nitrogen may be optionally substituted by a group Q;

m, p and q is 1, 2, 3, 4 or 5; wherein the definitions of $R^2$, $R^3$ and $R^4$ above may be the same or different;

$R^5$ is hydrogen, fluoromethyl, difluoromethyl, trifluoromethyl, $C_{1-6}$alkyl, $C_{2-6}$alkenyl, $C_{2-6}$alkynyl, $C_{0-6}$alkyl$C_{3-6}$cycloalkyl, $(CO)C_{1-6}$alkyl, $Cl_{1-6}$alkyl$NR^7R^8$;

$R^6$ is hydrogen $C_{1-6}$alkyl, $C_{2-6}$alkenyl, $C_{2-6}$alkynyl, trifluoromethyl;

$R^7$, $R^8$ is independently selected from hydrogen, $C_{1-6}$alkyl, $C_{0-6}$alkyl$C_{3-6}$cycloalkyl, $C_{2-6}$alkenyl, $C_{2-6}$alkynyl, $C_{0-6}$alkylaryl, $C_{0-6}$alkylheterocyclic group; wherein any $C_{1-6}$alkyl, $C_{2-6}$alkenyl, $C_{2-6}$alkynyl, $C_{0-6}$alkyl$C_{3-6}$cycloalkyl, aromatic group or heterocyclic group may be optionally substituted on carbon by one or more G and wherein $R^7$ and $R^8$ together may form a 5- or 6-membered heterocyclic group containing heteroatoms selected from N, O and S, wherein if said heterocyclic group contains an —NH— moiety that nitrogen may be optionally substituted by a group Q;

G and J are independently selected from hydrogen, halo, nitro, cyano, CHO, $OR^9$, $C_{1-6}$alkyl, $C_{2-6}$alkenyl, $C_{2-6}$alkynyl, $C_{0-6}$alkyl$C_{3-6}$cycloalkyl, fluoromethyl, difluoromethyl, trifluoromethyl, fluoromethoxy, difluoromethoxy, trifluoromethoxy, $NR^9R^{10}$, $CO_2R^9$, $CONR^9R^{10}$, $NR^9(CO)R^9$, $O(CO)R^9$, $COR^9$, $SR^9$, $(SO_2)NR^9R^{10}$, $(SO)NR^9R^{10}$, $SO_3R^9$, $SO_2R^9$, $SOR^9$;

$R^9$ and $R^{10}$ is independently selected from hydrogen and $C_{1-6}$alkyl and wherein $R^9$ and $R^{10}$ together may form a 5- or 6-membered heterocyclic group containing heteroatoms selected from N, O and S wherein if said heterocyclic group contains an —NH— moiety that nitrogen may be optionally substituted by a group Q;

Q is selected from $C_{1-4}$alkyl, $COC_{1-4}$alkyl, $SO_2C_{1-4}$alkyl, $(CO)OC_{1-4}$alkyl, $CONH_2$, $CONHC_{1-4}$alkyl, $CON(C_{1-4}$alkyl$)_2$, benzyl and benzyloxycarbonyl;

as a free base or a pharmaceutically acceptable salt thereof.

Further embodiments of the invention relates to compounds of formula I wherein X is $C_{0-2}$alkyl-U—$C_{0-2}$alkyl, where any $C_{1-2}$alkyl may be optionally substituted on a carbon atom by one or more G. Another embodiment of the invention relates to compounds, wherein X is U.

In another aspect of the invention Ring A is imidazo[1,2a]pyrid-3-yl.

In another aspect of the invention Ring B is pyridine or pyrimidine.

In a further aspect of the invention Ring B is pyrimidine.

In another aspect of the invention Ring C is a phenyl ring or a pyridine ring.

In a further aspect of the invention Ring C is a phenyl.

Listed below are defintions of various terms used in the specification and claims to describe the present invention.

For the avoidance of doubt it is to be understood that where in this specification a group is qualified by 'hereinbefore defined' or 'defined hereinbefore' the said group encompasses the first occurring and broadest definition as well as each and all of the preferred definitions for that group.

For the avoidance of doubt it is to be understood that in this specification '$C_{1-6}$' means a carbon group having 1, 2, 3; 4, 5 or 6 carbon atoms.

In this specification the term "alkyl" includes both straight and branched chain alkyl groups. The term $C_1$-$C_6$ alkyl having 1 to 6 carbon atoms and may be methyl, ethyl, n-propyl, i-propyl, n-butyl, i-butyl, s-butyl, t-butyl, n-pentyl, i-pentyl, t-pentyl, neo-pentyl, n-hexyl or i-hexyl. The term $C_1$-$C_3$ alkyl having 1 to 3 carbon atoms and may be methyl, ethyl, n-propyl or i-propyl. The term $C_1$-$C_2$ alkyl having 1 to 2 carbon atoms and may be methyl or ethyl.

A similar definition applies to other radicals, for example "phenyl$C_{1-6}$alkyl" includes phenyl$C_{1-4}$alkyl, 1-phenylethyl and 2-phenylethyl.

In the case where a subscript is the integer 0 (zero) the group to which the subscript refers to indicates that the group may be absent, i.e. there is a direct bond between the groups, for example in the definition of X which is $C_{0-6}$alkyl-U—$C_{0-6}$alkyl the subscript may be 0 (zero) which means that X=U.

The term "cycloalkyl" refers to an optionally substituted, saturated cyclic hydrocarbon ring system. The term "$C_{3-6}$cycloalkyl" may be cyclopropyl, cyclobutyl, cyclopentyl or cyclohexyl.

The term "alkenyl" refers to a straight or branched chain alkenyl group. The term $C_2$-$C_6$ alkenyl having 2 to 6 carbon atoms and one double bond, and may be vinyl, allyl, n-propenyl, i-propenyl, n-butenyl, i-butenyl, crotyl, pentenyl, i-pentenyl or hexenyl. The term $C_2$-$C_3$ alkenyl having 2 to 3 carbon atoms and one or two double bond, and may be vinyl, allyl, propenyl or i-propenyl.

The term "alkynyl" refers to a straight or branched chain alkynyl group. The term $C_2$-$C_6$ alkynyl having 2 to 6 carbon atoms and one trippel bond, and may be etynyl, propargyl, n-butynyl, i-butynyl, n-pentynyl, i-pentynyl or hexynyl. The term $C_2$-$C_3$ alkynyl having 2 to 3 carbon atoms and one trippel bond, and may be etenyl or propargyl.

The term "$C_{1-3}$alkoxy" may be straight or branched and may be methoxy, ethoxy, n-propoxy or i-propoxy.

The term "halo" refers to fluoro, chloro, bromo and iodo.

The term "aromatic group" refers to an optionally substituted monocyclic or bicyclic hydrocarbon ring system containing at least one unsaturated aromatic ring. The "aromatic group" may be fused with a $C_5$-$C_7$ cycloalkyl ring to form a bicyclic hydrocarbon ring system. Suitable examples of the term "aromatic group" are phenyl, naphthyl, indanyl and tetralinyl.

The term 5- or 6-membered heteroaromatic ring containing one, two or three heteroatoms selected from N, O and S may be furyl, imidazolyl, isoxazolyl, isothiazolyl, oxazolyl, pyrazinyl, pyrazolyl, pyridazinyl, pyridyl, pyrimidyl, pyrrolyl, thiazolyl or thienyl.

The term "heterocyclic group" refers to a saturated, partially saturated or unsaturated, mono or bicyclic ring containing 4 to 12 atoms of which at least one heteroatom is chosen from N, S or O, which may, unless otherwise specified, be carbon or nitrogen linked, wherein a $CH_2$ group can optionally be replaced by a CO, a ring nitrogen atom may optionally bear a $C_{1-6}$alkyl group and form a quaternary compound or a ring nitrogen and/or sulphur atom may be optionally oxidised to form the N-oxide, sulfoxide and/or sulfone. Suitable examples of the term "heterocyclic group" are morpholinyl, piperidyl, pyridyl, pyranyl, pyrrolyl, isothiazolyl, indolyl, quinolyl, thienyl, 1,3-benzodioxolyl, thiadiazolyl, piperazinyl, thiazolidinyl, pyrrolidinyl, thiomorpholino, pyrrolinyl, homopiperazinyl, 3,5-dioxapiperidinyl, tetrahydropyranyl, imidazolyl, pyrimidyl, pyrazinyl, pyridazinyl, isoxazolyl, N-methylpyrrolyl, 4-pyridone, 1-isoquinolone, 2-pyrrolidone, 4-thiazolidone, pyridine-N-oxide and quinoline-N-oxide. Particulary a "heterocyclic group" is a saturated, partially saturated or unsaturated, mono or bicyclic ring containing 5 or 6 atoms of which at least one heteroatom is chosen from nitrogen, sulphur or oxygen, which may, unless otherwise specified, be carbon or nitrogen linked, wherein a $CH_2$ group can optionally be replaced by a C(O), a ring nitrogen atom may optionally bear a $C_{1-6}$alkyl group and form a quaternary compound or a ring nitrogen and/or sulphur atom may be optionally oxidised to form the N-oxide and/or sulfoxide or sulfone.

Where optional substituents are chosen from "one or more" groups it is to be understood that this definition includes all substituents being chosen from one of the specified groups or the substituents being chosen from two or more of the specified groups.

A suitable pharmaceutically acceptable salt of a compound of the invention is, for example, an inorganic or organic acid, for example hydrochloric, hydrobromic, sulphuric, phosphoric, trifluoroacetic, citric or maleic acid. In addition a suitable pharmaceutically acceptable salt of a compound of the invention, is for example, an alkali metal salt, an alkaline earth metal salt, an ammonium salt or a salt with an organic base, which affords a physiologically-acceptable cation.

Some compounds of formula I may have chiral centres and/or geometric isomeric centres (E- and Z-isomers), and it is to be understood that the invention encompasses all such optical, diastereoisomeric and geometric isomers.

The invention also relates to any and all tautomeric forms of the compounds of the formula I.

Another embodiment of the invention is the following compounds:

2-[4-(4-Morpholinobenzoyl)anilino]-4-(imidazo-[1,2-a]-pyridin-3-yl)pyrimidine,

2-[4-(4-N,N-diethylcarbamoylbenzoyl)anilino]-4-(imidazo-[1,2-a]-pyridin-3-yl)pyrimidine, 2-[4-(4-Methylbenzoyl)anilino]-4-(imidazo-[1,2-a]-pyridin-3-yl)pyrimidine, 2-[4-(4-Cyanobenzoyl)anilino]-4-(imidazo-[1,2-a]-pyridin-3-yl)pyrimidine, 2-[4-(3-Chlorobenzoyl)anilino]-4-(imidazo-[1,2-a]-pyridin-3-yl)pyrimidine, 2-[4-(3-Ethoxybenzoyl)anilino]-4-(imidazo-[1,2-a]-pyridin-3-yl)pyrimidine, 2-(4-Benzoylanilino)-4-(imidazo-[1,2-a]-pyridin-3-yl)pyrimidine, (±)-2-[4-(Hydroxyphenylmethyl)anilino]-4-(imidazo-[1,2-a]-pyridin-3-yl)pyrimidine, 2-[4-(1-Oxo-2-phenylethyl)anilino]-4-(imidazo-[1,2-a]-pyridin-3-yl)pyrimidine, 2-(3-Benzoylanilino)-4-(imidazo-[1,2-a]-pyridin-3-yl)pyrimidine, 2-[4(1H-Indol-6-ylcarbonyl)anilino]-4-(imidazo-[1,2-a]-pyridin-3-yl)pyrimidine, 2-[4-(4,5-Dihydro-1H-pyrazol-4-ylcarbonyl)anilino]-4-(imidazo-[1,2-a]-pyridin-3-yl)pyrimidine, 2-[4-(1,3-Thiazol-2-ylcarbonyl)anilino]-4-(imidazo-[1,2-a]-pyridin-3-yl)pyrimidine.

Methods of Preparation

Another aspect of the present invention provides a process for preparing a compound of formula I as a free base or a pharmaceutically acceptable salt thereof. The process, (wherein $R^1$, $R^2$, $R^3$, $R^4$, X, Ring A, Ring C, Ring D, m, p, q and n are, unless otherwise specified, are as defined in formula I and Ring B is a pyrimidine or a pyridine wherein P is N or $CR^1$), comprising:

a) reacting of a pyrimidine or a pyridine of formula II:

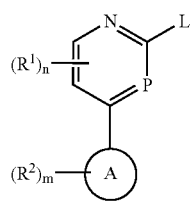

(II)

wherein L is an amine or a leaving group; with a compound of formula III wherein L is an amine or a leaving group:

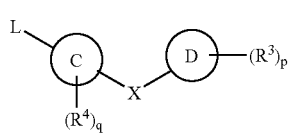

(III)

b) reacting a pyrimidine or a pyridine of formula IV:

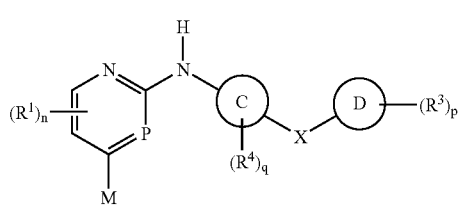

(IV)

with a compound of the formula V:

(V)

wherein one of M and $Q^1$ is a leaving group E and the other is a metallic group Y; or c) when P is N, reacting a compound of formula VI:

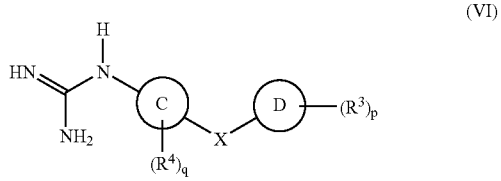

(VI)

with a compound of formula VII:

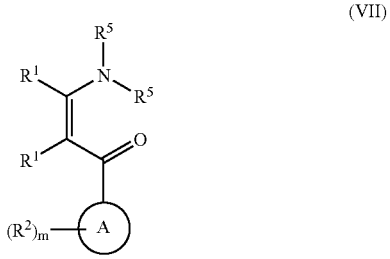

(VII)

wherein $R^5$ is $C_{1-6}$alkyl and $R^1$ is as defined above;

and thereafter, if necessary:

i) converting a compound of the formula I into another compound of the formula I e.g. reduction of X when X is CO to $C(OR^5)R^6$ wherein $R^5=R^6$=hydrogen.

ii) removing any protecting groups; and iii) forming a free base or a pharmaceutically acceptable salt thereof.

L is defined as an amino group or leaving groups. Suitable leaving groups are for example, a halo, sulphonyloxy group or a thio ether, for example a chloro, bromo, methanesulphonyloxy or a toluene4-sulphonyloxy group or a thiomethyl ether. One of the L is an amino group and the other is a leaving group.

A suitable leaving group E is, for example, a halo or sulphonyloxy group, for example a bromo, iodo or trifluoromethylsulphonyloxy group.

A suitable metallic group Y, is, for example, copper, lithium, an organoboron reagent such as $B(OH)_2$, $B(OPr^i)_2$ or $B(Et)_2$, or an organotin compound such as $SnBu_3$, an organosilicon compound such as $Si(Me)F_2$, an organozirconium compound such as $ZrCl_3$, an organoaluminium compound such as $AlEt_2$, an organomagnesium compound such as MgBr, an organozinc compound such as ZnCl or an organomercury compound such as HgBr.

Suitable reaction conditions for the above reactions are as follows:

a) A compound of formula II and a compound of formula III may be reacted together:

i) in the presence of a suitable solvent for example a ketone such as acetone or an alcohol such as ethanol or butanol or an aromatic hydrocarbon such as toluene or N-methyl pyrrolidine, optionally in the presence of a suitable base for example an inorganic base such as potassium carbonate or an organic base such as triethyl amine or sodium bis(trimethylsilyl)amide, or optionally in the presence of a suitable acid for example an inorganic acid such as hydrochloric acid or sulphuric acid, or an organic acid such as acetic acid or formic acid or a suitable Lewis acid and at a temperature in the range of 0° C. to reflux, preferably at reflux; or ii) in the presence of a suitable palladium catalyst such as $PdX_2$, $L^a{}_2Pd(0)$ or $L^a{}_2PdX_2$, where X stands for a halogen such as chlorine or bromine and $L^a$ stands for a suitable ligand such as triphenylphosphine, tri-o-tolylphosphine, trifurylphosphine, triphenylarsine or dibenzylidenacetone and with or without an addition of a ligand $L^b$ such as triphenylphosphine, tri-o-tolylphosphine, trifurylphosphine, 2,2'-bis(diphenylphosphino)-1,1'-binaphthalene (either as a racemate or as an enantiomer) or triphenylarsine in an suitable solvent such as dioxane, tetrahydrofuran, toluene, benzene, N,N-dimethylformamide or xylene in the presence of a suitable base such as cesium carbonate, sodium tert-butoxide or lithium bis(trimethylsilyl)amide and the reaction may occur at a temperature between ±20° C. and ±150° C.

A compound of the formula II may be prepared according to SCHEME I

SCHEME I

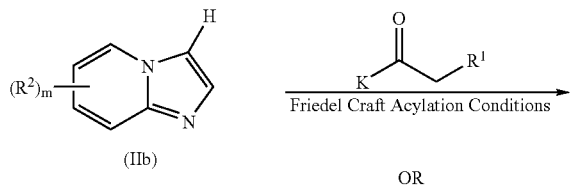

wherein one of M and $Q^2$ is a leaving group E as defined above and the other is a metallic group Y as defined above and L is as defined above.

Cross coupling conditions are well known in the art. Suitable conditions include, for example, those described under b) below.

Compounds of the formula II where Ring A is imidazo[1,2a]pyrid-3-yl and when P is N, may also be prepared according to SCHEME II.

SCHEME II

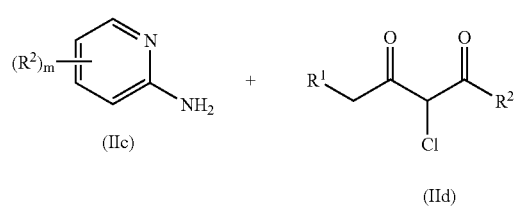

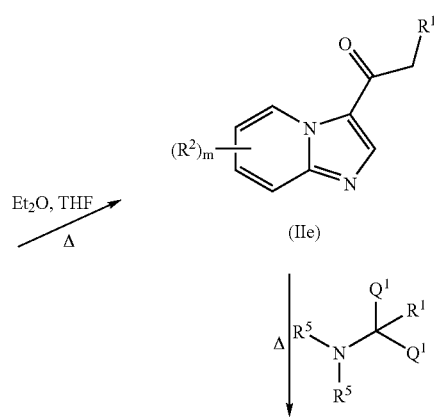

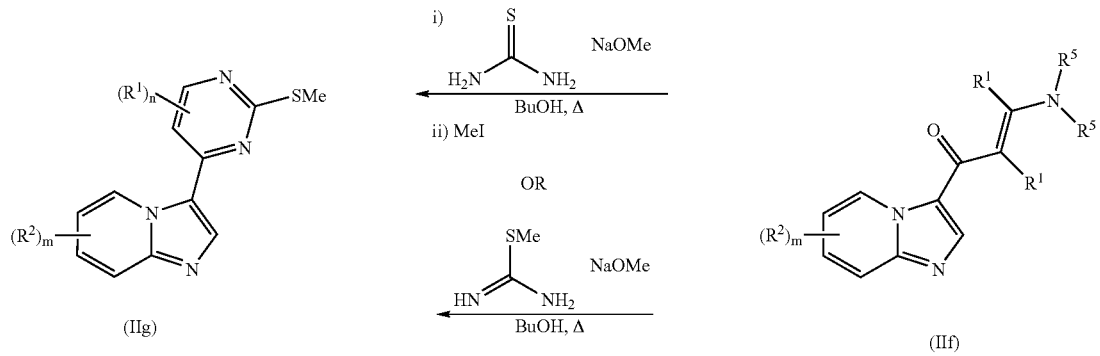

K is a suitable leaving group (for example $C_{1-6}$alkanoyloxy), $R^1$ and $R^2$ are as defined above, m is 0, 1, 2, 3 or 4; $Q^1$ is a suitable leaving group (for example $C_{1-6}$alkoxy) and $R^5$ is as defined above.

Where Ring A is pyrazolo[2,3a]pyrid-3-yl compounds of the formula II and when P is N, may also be prepared according to SCHEME III.

SCHEME III

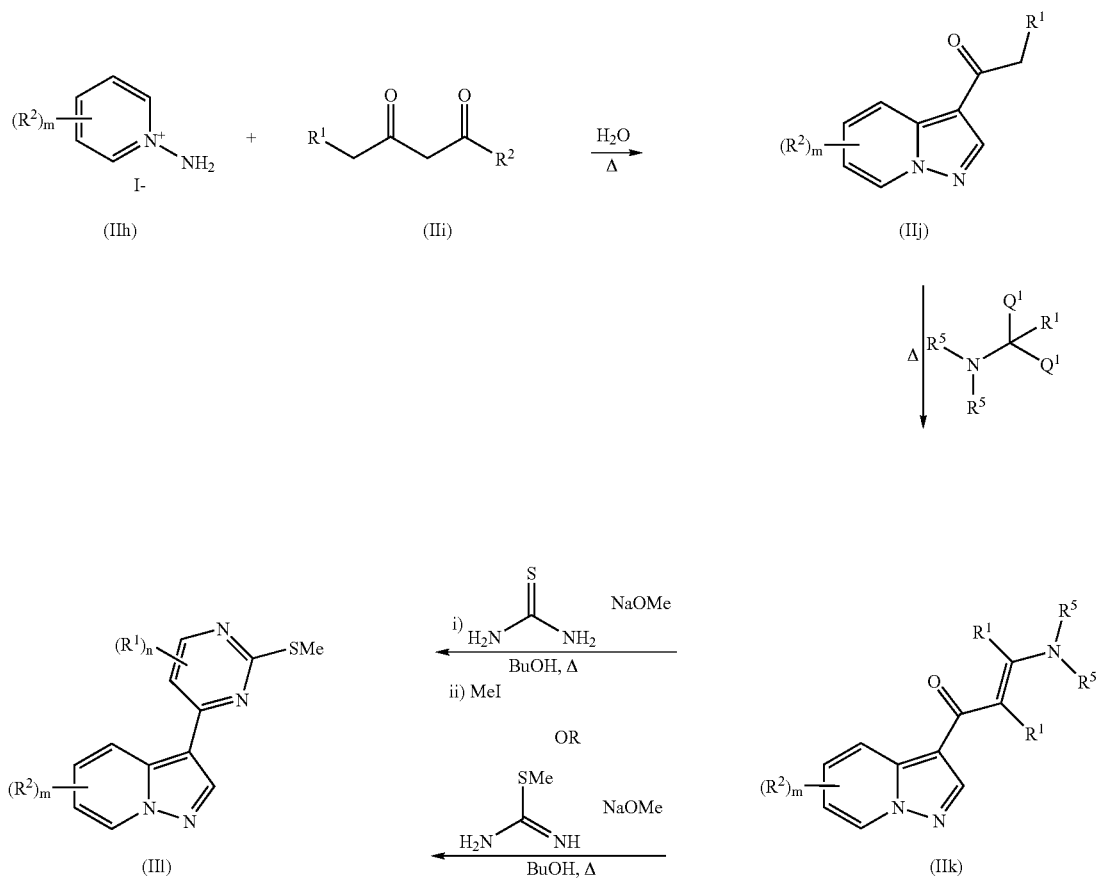

wherein $Q^1$, $R^1$, $R^2$ and $R^5$ are as defined above.

Compounds of formula IIf or IIk may be further modified to produce compounds of formula IIn:

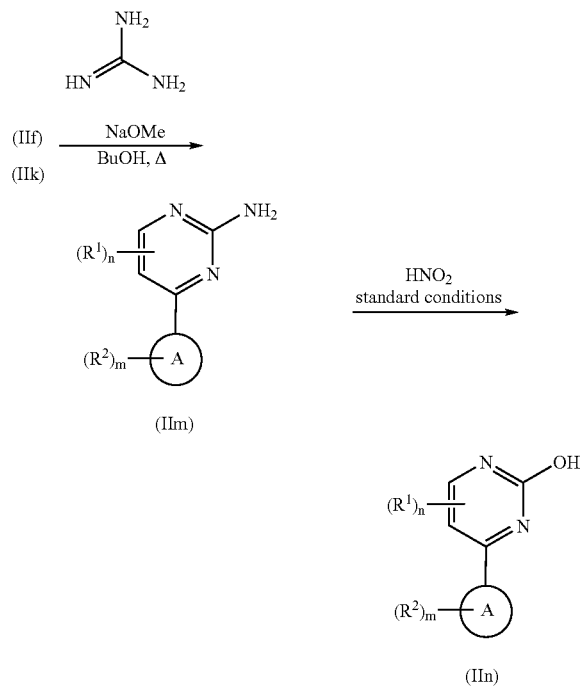

It will be appreciated by those skilled in the art that compounds of formula IIn may be additionally modified by standard functional group modification reactions known in the art to produce compounds of formula II where L is as defined above.

Compounds of formula III, where X is —CO—, may be prepared according to SCHEME V,

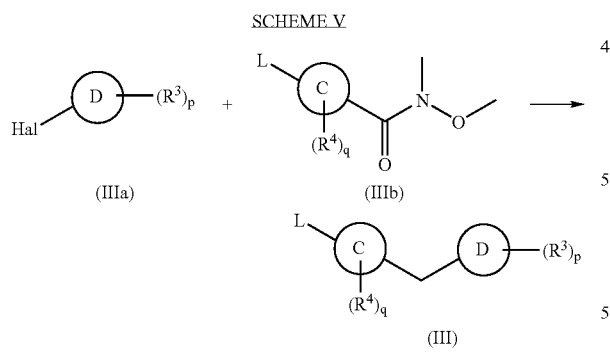

by a metal-halogen exchange reaction, in an appropriate anhydrous solvent such as tetrahydrofuran or diethyl ether using a suitable alkyl-lithium or metal e.g. butyllithium, lithium or magnesium turnings, of a compound of formula IIIa, wherein Hal is Cl, Br or I, followed by reaction with a compound of formula IIIb, wherein L is as defined above. The reaction may be performed at a reaction temperature within the range of −78° C. to room temperature.

Compounds of formula IIa, IIb, IIc, IId, IIh, IIi, IIIa and IIIb are commercially available compounds, or they are known in the literature, or they are prepared by standard processes known in the art.

b) Compounds of formula IV and compounds of formula V may be reacted together under standard cross coupling conditions. Examples of these are in the presence of a catalyst, for example, a metallic catalyst such as tetrakis(triphenylphosphine)palladium(0), palladium(II) chloride, palladium(II) bromide, nickel(II) chloride, nickel(II) bromide or bis(triphenylphosphine)nickel(II) chloride, in the presence of a suitable inert solvent or diluent, for example tetrahydrofuran, 1,4-dioxan, 1,2-dimethoxyethane, benzene, toluene, xylene, methanol or ethanol. The reaction is preferably conducted in the presence of a suitable base such as, for example, sodium carbonate or potassium carbonate, pyridine, 4-dimethylaminopyridine, triethylamine or morpholine, and conveniently at a temperature in the range of, for example 10 to 250° C., preferably in the range of 60 to 120° C.

Compounds of formula IV may be prepared according to SCHEME VI One of the L is an amino group and the other L is a leaving group.

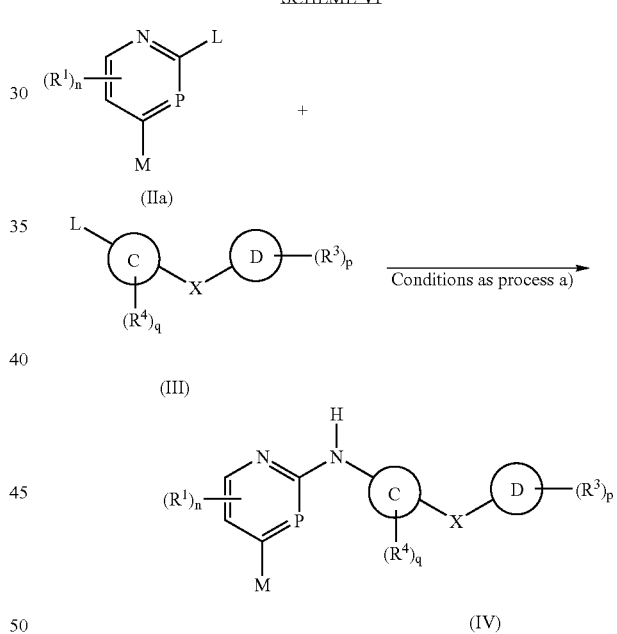

Compounds of formula V are commercially available compounds, or they are known in the literature, or they are prepared by standard processes known in the art.

c) Compounds of formula VI and compounds of formula VII are reacted together in a suitable solvent such as N-methylpyrrolidinone or butanol at a temperature in the range of 100 to 200° C., preferably in the range of 150 to 170° C. The reaction is preferably conducted in the presence of a suitable base such as, for example, sodium methoxide or potassium carbonate.

Compounds of formula VI and VII are commercially available compounds, or they are known in the literature, or they are prepared by standard processes known in the art, or compounds of formula VII may be prepared by a process similar to that described for IIf and IIk hereinabove.

It will be appreciated that certain of the various ring substituents in the compounds of the present invention may be introduced by standard aromatic substitution reactions or generated by conventional functional group modifications either prior to or immediately following the processes mentioned above, and as such are included in the process aspect of the invention. Such reactions and modifications include, for example, introduction of a substituent by means of an aromatic substitution reaction, reduction of substituents, alkylation of substituents and oxidation of substituents. The reagents and reaction conditions for such procedures are well known in the chemical art. Particular examples of aromatic substitution reactions include the introduction of a nitro group using concentrated nitric acid, the introduction of an acyl group using, for example, an acyl halide and Lewis acid (such as aluminium trichloride) under Friedel Crafts conditions; the introduction of an alkyl group using an alkyl halide and Lewis acid (such as aluminium trichloride) under Friedel Crafts conditions; and the introduction of a halogeno group. Particular examples of modifications include the reduction of a nitro group to an amino group by for example, catalytic hydrogenation with a nickel catalyst or treatment with iron in the presence of hydrochloric acid with heating; oxidation of alkylthio to alkylsulphinyl or alkylsulphonyl. It will also be appreciated that in some of the reactions mentioned herein it may be necessary/desirable to protect any sensitive groups in the compounds. The instances where protection is necessary or desirable, suitable methods for protection are known to those skilled in the art. Conventional protecting groups may be used in accordance with standard practice (for illustration see T. W. Green, P. G. M. Wutz, Protective Groups in Organic Synthesis, Wiley Interscience, 1999). The protecting groups may be removed at any convenient stage in the synthesis using conventional techniques well known in the chemical art.

Intermediates

The invention is further directed to a compound of formula III

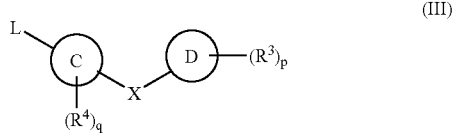

(III)

wherein X, Ring C, Ring D, $R^3$, $R^4$, p and q are as defined in formula I and L is an amine, or a leaving group. Further values of X is CO or $C(OR^5)R^6$ and of Ring C is phenyl.

WORKING EXAMPLES

The following examples will describe, but not limit, the invention and unless otherwise:
(i) temperatures are given in degrees Celsius (° C.);
(ii) organic solutions were dried over anhydrous magnesium sulphate or anhydrous sodium sulphate;
(iii) chromatography means flash chromatography on silica gel; thin layer chromatography (TLC) was carried out on silica gel plates;
(iv) in general, the course of reactions was followed by TLC and reaction times are given for illustration only;
(v) final products had satisfactory proton and/or carbon nuclear magnetic resonance (NMR) spectra and/or mass spectral data;
(vi) yields are given for illustration only and are not necessarily those which can be obtained by diligent process development; preparations were repeated if more material was required;
(vii) when given, NMR data is in the form of delta values for protons, given in parts per million (ppm) relative to tetramethylsilane (TMS) as an internal standard, determined at 300 MHz or a 400 MHz using perdeuterio dimethyl sulphoxide (DMSO-$d_6$) or deuterio chloroform (CDCl$_3$) as solvent unless otherwise indicated;
(viii) chemical symbols have their usual meanings; SI units and symbols are used;
(ix) solvent ratios are given in volume:volume (v/v) terms; and
(x) mass spectra were run with an electron energy of 70 electron volts in the chemical ionization (CI) mode; where indicated ionization was effected by electron impact (EI), fast atom bombardment (FAB) or electrospray (ESP); if not otherwise indicated values for m/z are given; generally, only ions which indicate the parent mass are reported;
(xi) unless stated otherwise, compounds containing an asymmetrically substituted carbon and/or sulphur atom have not been resolved;

Example 1

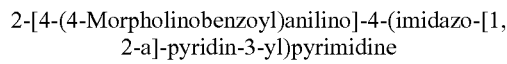

A mixture of sodium tert-butoxide (31 mg, 0.32 mmol), palladium acetate (3 mg, 0.013 mmol), and (S)-BINAP (11 mg, 0.018 mmol) in toluene (2 mL) was stirred at room temperature for 0.5 h. A warm suspension of 2-amino-4-(imidazo[1,2-a]pyridin-3-yl)pyrimidine (58 mg, 0.27 mmol) in toluene (4 mL) and 4-bromo-4'-morpholinobenzophenone (79 mg, 0.23 mmol) was added, and the mixture was heated at 100° C. for 4 h. The solvent was removed in vacuo, and the residue was partitioned between dichloromethane and water. The phases were separated and the organic layer was washed with brine, dried (MgSO$_4$) and the solvent was removed in vacuo. The crude product was purified by column chromatography on silica gel using chloroform/ethanol, 98:2, as the eluent affording 25 mg (23% yield) of the title compound as a yellow solid: mp (decomp.) >237° C.; $^1$H NMR (400 MHz, DMSO-$d_6$) δ 10.18 (d, J=6.8 Hz, 1 H), 10.1 (s, 1 H), 8.68 (s, 1 H), 8.53 (d, J=5.4 Hz, 1 H), 7.96 (d, J=8.5 Hz, 2 H), 7.80 (d, J=8.9 Hz, 1 H), 7.73 (d, J=8.6 Hz, 2 H), 7.69 (d, J=8.7 Hz, 2 H), 7.56-7.51 (m, 2 H), 7.19 (t, J=6.8 Hz, 1 H), 7.05 (d, J=8.7 Hz, 2 H), 3.76 (s, 4 H), 3.33 (s, 4 H); $^{13}$C NMR (400 MHz, DMSO-$d_6$) δ 193.0, 159.4, 157.6, 157.3, 153.9, 148.3, 144.3, 139.3, 131.9, 131.1, 131.0, 129.7, 127.5, 127.4, 121.3, 118.2, 117.7, 114.2, 113.3, 108.4, 66.2, 47.2; MS (TSP) 7 m/z 477 (M+1).

Example 2

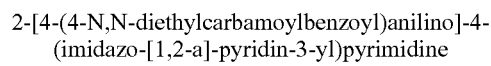

A mixture of 2-amino4(imidazo[1,2-a]pyridin-3-yl)pyrimidine (56 mg, 0.26 mmol), 4-(4-bromobenzoyl)-N,N-diethylbenzamide (95 mg, 0.26 mmol), cesium carbonate (120 mg, 0.37 mmol), palladium acetate (3 mg, 0.013 mmol), and (S)-BINAP (12 mg, 0.020 mmol) in N,N-dimethylformamide (2.5 mL) was stirred at 100° C. under nitrogen for 6 h. The solvent was removed in vacuo, and the residue was partitioned between dichloromethane and water. The phases were separated and the organic layer was washed with brine; dried (MgSO$_4$) and the solvent was removed in vacuo. The crude product was purified by column chromatography on silica gel using chloroform/ethanol, 98:2, as the eluent affording 29 mg (22% yield) of the title compound as a yellow solid: mp 172-174° C.; $^1$H NMR (400 MHz, CDCl$_3$) δ 9.88 (d, J=6.7 Hz, 1 H), 8.47 (d, J=5.2 Hz, 1 H), 8.33 (s, 1 H), 7.91-7.74 (m, 7 H), 7.61 (s, 1 H), 7.49 (d, J=7.5 Hz, 2 H), 7.40 (t, J=7.8 Hz, 1 H), 7.21 (d, J=5.1 Hz, 1 H), 6.99 (t, J=6.8 Hz, 1 H), 3.65-3.50 (m, 2 H), 3.35-3.20 (m, 2 H), 1.35-1.20 (m, 3 H), 1.20-1.05 (m, 3 H); $^{13}$C NMR (400 MHz, CDCl$_3$) δ 194.9, 170.4, 159.1, 157.6, 157.5, 148.8, 144.0, 140.6, 138.8, 138.4, 131.9, 130.9, 129.9, 128.8, 126.9, 126.2, 121.5, 118.4, 118.0, 113.8, 108.8, 43.3, 39.3, 14.3, 12.9; MS (ESP) m/z 491 (M+1).

Example 3

2-[4-(4-Methylbenzoyl)anilino)-4-(imidazo-[1,2-a]-pyridin-3-yl)pyrimidine

The title compound was prepared from 2-amino-4-(imidazo[1,2-a]pyridin-3-yl)pyrimidine and 4-bromo4'-methylbenzophenone following the general method of Example 2. The crude product was purified by column chromatography on silica gel using chloroform/ethanol, 98:2, as the eluent affording 52 mg (17% yield) of the title compound as a yellow solid: mp 238.9-239.2° C.; $^1$H NMR (400 MHz, DMSO-d$_6$) δ 10.15-10.13 (m, 2 H), 8.64 (s, 1 H), 8.50 (d, J=5.3 Hz, 1 H), 7.96 (d, J=8.5 Hz, 2 H), 7.79-7.74 (m, 3 H), 7.63 (d, J=7.8 Hz, 2 H), 7.53-7.49 (m, 2 H), 7.35 (d, J=7.7 Hz, 2 H), 7.16 (t, J=6.8 Hz, 1 H), 2.40 (s, 3 H); $^{13}$C NMR (400 MHz, DMSO-d$_6$) δ 194.4, 159.4, 157.7, 157.4, 148.4, 145.1, 142.7, 139.4, 135.5, 131.5, 130.1, 129.9, 129.8, 129.3, 127.5, 121.3, 118.2, 117.8, 114.2, 108.6, 21.5; MS (TSP) m/z 406 (M+1).

Example 4

2-[4-(4-Cyanobenzoyl)anilino]-4-(imidazo-[1,2-a]-pyridin-3-yl)pyrimidine

The title compound was prepared from 2-amino-4-(imidazo[1,2-a]pyridin-3-yl)pyrimidine and 4-bromo-4'-cyanobenzophenone following the general method of Example 2. The crude product was purified by washing with water, diethyl ether, ethyl acetate, and finally dichloromethane affording 184 mg (63% yield) as a yellow solid: mp (decomp.) >230° C.;

$^1$H NMR (400 MHz, DMSO-d$_6$) δ 10.45-10.20 (broad s, 1 H), 10.18 (d, J=6.9 Hz, 1 H), 8.67 (s, 1 H), 8.53 (d, J=5.4 Hz, 1 H), 8.04 (d, J=8.2 Hz, 2 H), 8.00 (d, J=8.7 Hz, 2 H), 7.86 (d, J=8.2 Hz, 2 H), 7.81-7.78 (m, 3 H), 7.56-7.51 (m, 2 H), 7.19 (t, J=6.7 Hz, 1 H); $^{13}$C NMR (400 MHz, DMSO-d$_6$) δ 194.8, 160.9, 159.0, 158.8, 149.8, 148.0, 143.9, 140.8, 134.2, 133.3, 131.4, 131.3, 129.9, 128.9, 122.7, 120.1, 119.8, 119.1, 115.7, 115.6, 110.0; MS (ESP) m/z 417 (M+1).

Example 5

2-[4-(3-Chlorobenzoyl)anilino]-4-(imidazo-[1,2-a]-pyridin-3-yl)pyrimidine

The title compound was prepared from 2-amino-4-(imidazo-[1,2-a]pyridin-3-yl)pyrimidine and 4-bromo-3'-chlorobenzophenone following the general method of Example 2. The crude product was purified by column chromatography on silica gel using chloroform/ethanol, 99:1, as the eluent affording 51 mg (21% yield) of the title compound as a yellow solid: mp 194.7-196.7° C.; $^1$H NMR (400 MHz, DMSO-d$_6$) δ 10.26 (s, 1 H), 10.17 (d, J=7.0 Hz, 1 H), 8.69 (s, 1 H), 8.54 (d, J=5.4 Hz, 1 H), 8.01 (d, J=8.7Hz, 2 H), 7.83-7.79 (m, 3 H), 7.76-7.72 (m, 2 H), 7.70-7.66 (m, 1 H), 7.62-7.59 (m, 1 H), 7.56-7.51 (m, 2 H), 7.21 (t, J=6.9 Hz, 1 H); $^{13}$C NMR (400 MHz, DMSO-d$_6$) δ 193.2, 159.3, 157.7, 157.4, 148.4, 145.7, 140.4, 139.4, 133.7, 132.0, 131.8, 130.8, 129.8, 129.1, 129.0, 128.3, 127.6, 121.3, 118.3, 117.8, 114.3, 108.8; MS (ESP) m/z 426 (M+1).

Example 6

2-[4-(3-Ethoxybenzoyl)anilino]-4-(imidazo-[1,2-a]-pyridin-3-yl)pyrimidine

The title compound was prepared from 2-amino-4-(imidazo-[1,2-a]pyridin-3-yl)pyrimidine and 4-bromo-3'-ethoxybenzophenone following the general method of Example 2. The crude product was purified by column chromatography on silica gel using chloroform/ethanol, 98:2, as the eluent affording 0.11 g (48% yield) of the title compound as a yellow solid: mp 197.3-197.5° C.; $^1$H NMR (400 MHz, DMSO-d$_6$) δ 10.21 (s, 1 H), 10.17 (d, J=6.8 Hz, 1 H), 8.68 (s, 1 H), 8.53 (d, J=5.4 Hz, 1 H), 8.00 (d, J=8.5 Hz, 2 H), 7.82-7.79 (m, 3 H), 7.55-7.51 (m, 2 H), 7.47 (t, J=8.2 Hz, 1 H), 7.28 (d, J=7.5 Hz, 1 H), 7.23-7.17 (m, 3 H), 4.10 (q, J=6.8 Hz, 2 H), 1.36 (t, J=6.9 Hz, 3 H); $^{13}$C NMR (400 MHz, DMSO-d$_6$) δ 194.4, 159.4, 158.7, 157.6, 157.4, 148.4, 145.4, 139.7, 139.4, 131.6, 129.9, 129.8, 129.8, 127.5, 22.0, 121.3, 118.6, 118.2, 117.8, 114.8, 114.2, 108.6, 63.6, 15.0; MS (ESP) m/z 436 (M+1).

Example 7

2-(4-Benzoylanilino)-4-(imidazo-[1,2-a]-pyridin-3-yl)pyrimidine

The title compound was prepared from 2-amino-4-(imidazo-[1,2-a]pyridin-3-yl)pyrimidine and 4-bromobenzophenone following the general method of Example 1 using cesium carbonate as the base and tris(dibenzylideneacetone) dipalladium (0) as the palladium source. The crude product was purified by column chromatography on silica gel using chloroform/ethanol, 95:5, as the eluent affording 0.14 g (58% yield) of the title compound as a yellow solid: mp (decomp.) 249-255° C.; MS (TSP) m/z 392 (M+1 ), $^1$H NMR (400 MHz, DMSO-d$_6$) δ 10.38 (s, 1 H), 10.35 (d, J=6.8 Hz, 1 H), 9.03 (s, 1 H), 8.67 (d, J=5.4 Hz, 1 H), 8.01 (d, J=8.7 Hz, 2 H), 7.98 (m, 1 H), 7.87 (m, 1 H), 7.83 (d, J=8.7 Hz, 2 H), 7.76 (d, J=7.0 Hz; 2 H), 7.69 (m, 1 H), 7.59 (m, 3 H), 7.47 (m, 1 H).

Example 8

(±)-2-[4-(Hydroxyphenylmethyl)anilino]-4-(imidazo-[1,2-a]-pyridin-3-yl)pyrimidine Sodium borohydride (9 mg, 0.24 mmol) was added in one portion to a suspension of 2-(4-benzoylanilino)-4-(imidazo-[1,2-a]-pyridin-3-yl)-pyrimidine (27 mg, 0.069 mmol) in methanol (2 mL). The mixture was stirred at room temperature for 63 hours. HCl (5 mL, 1 M) was added and the mixture was stirred for another 15 min. After evaporation of the solvent in vacuo, the residue was suspended in water and extracted with chloroform. The phases were separated and the organic phase was dried ($MgSO_4$) and the solvent was evaporated in vacuo. The crude material was purified on a silica gel column using chloroform/EtOH, 95:5, as the eluent to give 24 mg (88% yield) of the product as a pale yellow solid: mp 213-216° C.; MS (TSP) m/z 394 (M+1), $^1$H NMR (400 MHz, DMSO-$d_6$) δ 9.87 (d, J=5.9 Hz, 1 H), 9.43 (s, 1 H), 8.43 (s, 1 H), 8.23 (d, J=5.48 Hz, 1 H), 7.58 (d, J=9.0 Hz, 1 H), 7.46 (d, J=8.4 Hz, 2 H), 7.29 (m, 1 H), 7.23 (m, 2 H), 7.20 (d, J=5.5 Hz, 1 H), 7.14 (m, 4 H), 7.04 (m, 1 H), 6.88 (m, 1 H), 5.51 (s, 1 H).

Example 9

2-[4-(1-Oxo-2-phenylethyl)anilino]-4-(imidazo-[1,2-a]-pyridin-3-yl)pyrimidine

The title compound was prepared from 2-amino-4-(imidazo[1,2-a]pyridin-3-yl)pyrimidine and benzyl 4-bromophenyl ketone following the general method of Example 2. The crude product was purified by column chromatography on silica gel using chloroform/ethanol, 98:2, as the eluent followed by recrystallization from acetonitrile affording 30 mg (10% yield) of the title compound as an off-white solid: mp (decomp.) 225-228° C.; $^1$H NMR (400 MHz, DMSO-$d_6$) δ 10.15 (broad s, 2 H), 8.67 (s, 1 H), 8.53 (d, J=5.3 Hz, 1 H), 8.06 (d, J=7.3 Hz, 2 H), 7.95 (d, J=7.3 Hz, 2 H), 7.80 (d, J=8.7 Hz, 1 H), 7.54-7.51 (m, 2 H), 7.32-7.16 (m, 6 H), 4.33 (s, 2 H); $^{13}$C NMR (400 MHz, DMSO-$d_6$) δ 195.8, 158.9, 157.2, 156.9, 148.0, 145.1, 138.9, 135.5, 129.7, 129.5, 129.3, 129.2, 128.2, 127.1, 126.3, 120.9, 117.9, 117.3, 113.8, 108.2, 44.3; MS (ESP) m/z 406 (M+1).

Example 10

2-(3-Benzoylanilino)-4-(imidazo-[1,2-a]-pyridin-3-yl)pyrimidine

To a solution of 2-methylsulfanyl-4-(imidazo-[1,2-a]pyridin-3-yl)pyrimidine (0.146 g, 0.60 mmol) and 3-aminobenzophenone (0.238 g, 1.21 mmol) in N,N-dimethylformamide (2.5 mL) was added sodium hydride (0.061 g, 1.52 mmol) and the mixture was heated at 130° C. for 4 hours. The mixture was allowed to cool to room temperature and the solvent was removed. The residue was dissolved in water and the resulting solid was washed with water and chloroform. The organic phase was dried over $MgSO_4$ and the solvent was evaporated. The crude product was purified by column chromatography on silica gel using chloroform/ethanol, 9:1, as the eluent affording 0.028 g (12% yield) of the title compound as a yellow solid: mp (decomp.) 237-246° C.; MS (TSP) m/z 392 (M+1); $^1$H NMR (400 MHz, DMSO-$d_6$) δ 10.25 (d, J=6.3 Hz, 1 H), 10.15 (s, 1 H), 8.74 (s, 1 H), 8.55 (d, J=5.4 Hz, 1 H), 8.29 (s, 1 H), 8.25 (d, J=8.1 Hz, 1 H), 7.87 (m, 3 H), 7.78 (t, J=7.4 Hz, 1 H), 7.67 (m, 2 H), 7.60 (m, 2 H), 7.55 (d, J=5.4 Hz, 1 H), 7.44 (d, J=7.5 Hz, 1 H), 7.20 (m, 1 H).

Example 11

2-[4-(1 H-Indol-6-ylcarbonyl)anilino]-4-(imidazo-[1,2-a]-pyridin-3-yl)pyrimidine The title compound was prepared from 2-amino-4-(imidazo-[1,2-a]pyridin-3-yl)pyrimidine and (4-bromophenyl)(1H-indol-5-yl)methanone following the general method of Example 1 using cesium carbonate as the base and tris(dibenzylideneacetone)dipalladium (0) as the palladium source. The crude product was purified by column chromatography on silica gel using chloroform/ethanol, 95:5, as the eluent affording 0.021 g (25% yield) of the title compound as a yellow solid: mp (decomp.) 173-178 ° C.; MS (TSP) m/z 431 (M+1); $^1$H NMR (400 MHz, DMSO-$d_6$) δ 11.58 (br s, 1 H), 10.27 (d, J=7.0 Hz, 1 H), 10.24 (s, 1 H), 8.77 (s, 1 H), 8.62 (d, J=5.4 Hz, 1 H), 8.07 (d, J=8.7 Hz, 2 H), 7.94 (s, 1 H), 7.89 (d, J=8.7 Hz, 2 H), 7.78 (d, J=8.3 Hz, 1 H), 7.71 (d, J=2.8 Hz, 1 H), 7.61 (m, 2 H), 7.57 (dd, J=8.2 Hz, J=1.3 Hz, 1 H), 7.28 (t, J=6.7 Hz, 1 H), 6.65 (d, J=2.7 Hz, 1 H); $^{13}$C NMR (100.5 MHz, DMSO-$d_6$) δ195.1, 159.5, 157.7, 157.4, 148.4, 144.5, 139.4, 135.3, 131.4, 131.1, 130.8, 129.8, 129.6, 127.5, 121.3, 120.8, 120.1, 118.2, 117.8, 114.9, 114.3, 108.5, 101.9.

Example 12

2-[4-(4,5-Dihydro-1H-pyrazol-4-ylcarbonyl)anilino]-4-(imidazo-[1,2-a]-pyridin-3-yl)pyrimidine The title compound was prepared from 2-amino-4-(imidazo-[1,2-a]pyridin-3-yl)pyrimidine and (4-bromophenyl)(1H-pyrazol-4-yl)methanone following the general method of Example 1 using potassium tert-butoxide as the base. The crude product was purified by column chromatography on silica gel using chloroform/ethanol, 95:5, as the eluent affording 0.020 g (8% yield) of the title compound as a yellow solid: mp (decomp.) 229-232° C.; MS (TSP) m/z 382 (M+1); $^1$H NMR (400 MHz, DMSO-$d_6$) δ 10.27 (d, J=6.9 Hz, 1 H), 10.21 (s, 1 H), 8.76 (s, 1 H), 8.62 (d, J=5.4 Hz, 1 H), 8.30 (br s 2H), 8.03 (m, 5 H), 7.89 (m, 1 H), 7.62 (m, 2 H), 7.29 (m, 1 H).

Example 13

2-[4-(1,3-Thiazol-2-ylcarbonyl)anilino]-4-(imidazo-[1,2-a]-pyridin-3-yl)pyrimidine The title compound was prepared from 2-amino-4-(imidazo-[1,2-a]pyridin-3-yl)pyrimidine and (4-bromophenyl)(1,3-thiazol-2-yl)methanone following the general method of Example 1 using cesium carbonate as the base and tris(dibenzylideneacetone)dipalladium (0) as the palladium source. The crude product was purified by column chromatography on silica gel using chloroform/ethanol, 95:5, as the eluent affording 0.126 g (45% yield) of the title compound as a yellow solid: mp (decomp.) 234-235° C.; MS (TSP) m/z 399 (M+1);

$^1$H NMR (400 MHz, $CDCl_3$) δ 10.52 (s, 1 H), 10.41 (d, J=7.0 Hz, 1 H), 8.92 (s, 1 H), 8.79 (d, J=5.4 Hz, 1 H), 8.75 (m, 2 H), 8.48 (dd, J=5.6 Hz, J=3.0 Hz, 2 H), 8.26 (m, 2 H), 8.03 (d, J=8.9 Hz, 1 H), 7.79 (d, J=5.5 Hz, 1 H), 7.76 (m, 1 H), 7.44 (m, 1 H).

Preparation of Starting Materials

The starting materials for the Examples above are either commercially available or are readily prepared by standard methods from known materials. For example the following reactions are illustrations but not limitations of the preparation of some starting materials used in the above reactions.

Method 1

4-Bromo-4'-morpholinobenzophenone

A solution of n-butyllithium in hexane (1.6 M, 0.49 mL, 0.79 mmol) was added dropwise to a solution of 4-(4-bromophenyl)morpholine (191 mg, 0.79 mmol; described in: Jones, D. H. J. Chem. Soc. (C), 1971, 132-137 ) in tetrahydrofuran (5 mL) under nitrogen at −78° C. After 10 minutes, a pre-cooled solution (−78° C.) of 4-bromo-N-methoxy-N-methylbenzamide (212 mg, 0.87 mmol; described in: Turnbull, K. Tet. Lett. 1998 39(12), 1509-12) in tetrahydrofuran (3 mL) was added via a double-tipped needle. The mixture was stirred at −78° C. for 5 min. The cooling bath was removed and the mixture was allowed to reach ambient temperature under 30 min. The solvent was removed in vacuo, and the residue was partitioned between ethyl acetate and water. The phases were separated and the organic layer was washed with brine, dried (MgSO$_4$) and the solvent was removed in vacuo. The crude product was purified by column chromatography on silica gel using heptane/ethyl acetate, 70:30, as the eluent affording 86 mg (32% yield) of the title compound as colorless crystals: mp 177.8-179.2° C.; $^1$H NMR (400 MHz, CDCl$_3$) δ 7.77 (d, J=9.0 Hz, 2 H), 7.61 (s, 4 H), 6.89 (d, J=9.0 Hz, 2 H), 3.89-3.85 (m, 4 H), 3.35-3.32 $^{13}$C NMR(400 MHz, CDCl$_3$) δ 194.5, 154.6, 137.8, 132.8, 131.8, 131.6, 127.7, 126.8, 113.6, 67.0, 47.9; MS (TSP) m/z 346 (M+1).

Method 2

4-(4-Bromobenzoyl)-N,N-diethylbenzamide

To a suspension of 4-(4-bromobenzoyl)benzoic acid (87 mg, 0.29 mmol; described in: Parham, W. E.; Sayed, Y. A. J. Org. Chem. 1974, 39(14), 2053-2056) in thionyl chloride (1 mL) at 50° C. was added a few drops of N,N-dimethylformamide. The clear solution was stirred at 50° C. for 30 min. The excess of thionyl chloride was removed under reduced pressure, and by evaporation with several portions of toluene. The residue was dissolved in dichloromethane (10 mL) and a large excess of triethylamine was added until basic pH. A solution of diethylamine (23 mg, 0.31 mmol) in dichloromethane (2 mL) was added and the mixture was stirred at room temperature for 3.5 h. The red solution was partitioned between water and additional dichlorormethane. The phases were separated and the organic layer was washed with brine, dried (MgSO$_4$) and the solvent was removed in vacuo. The crude product was purified by column chromatography on silica gel using heptane/ethyl acetate, 70:30, affording 70 mg (68% yield) of the title compound as a colorless oil, which partly solidified upon standing in refrigerator: $^1$H NMR (400 MHz, CDCl$_3$) δ 7.80 (d, J=8.3 Hz, 2 H), 7.70-7.63 (m, 4 H), 7.49 (d, J=8.1 Hz, 2 H), 3.59-3.57 (m, 2 H), 3.27-3.25 (m, 2 H), 1.30-1.25 (m, 3 H), 1.15-1.11 (m, 3 H); $^{13}$C NMR (400 MHz, CDCl$_3$) δ 195.4, 170.5, 141.7, 138.0, 136.3, 132.2, 132.0, 130.5, 128.3, 126.7, 43.7, 39.7, 14.7, 13.3; MS (ESP) m/z 360 (M+1).

Method 3

4-Bromo-3'-ethoxybenzophenone

The title compound was prepared from 3-bromophenetole and 4-bromo-N-methoxy-N-methylbenzamide following the general method of Method 1. The crude product was re-crystallized from methanol affording 0.37 g (47% yield) of the title compound as colorless crystals: mp 68.5-70.1° C.; $^1$H NMR (400 MHz, CDCl$_3$) δ 7.70-7.60 (m, 4 H), 7.38 (broad t, J=7.6 Hz, 1 H), 7.31-7.27 (m, 2 H), 7.13 (ddd, J=8.2, J=2.3, J=1.2 Hz, 1 H), 4.08 (q, J=7.0 Hz, 2 H), 1.43 (t, J=7.0 Hz, 3 H); $^{13}$C NMR (400 MHz, CDCl$_3$) δ 195.5, 159.0, 138.4, 136.4, 131.6, 131.5, 129.3, 127.5, 122.5, 119.5, 114.9, 63.7, 14.7; MS (TSP) m/z 305 (M+1).

Method 4

(4-Bromophenyl)(1H-indol-6-yl)methanone

To hexane washed potassium hydride (0.30 g, 1.5 mmol), suspended in anhydrous diethylether (1.5 mL), was added 5-bromoindole (0.241 g, 1.23 mmol) dissolved in diethyl ether (2.0 mL) at 0° C. After 15 min, the mixture was cooled to −78 ° C. and tert-buthyllithium (1.5 mL, 2.55 mmol), pre-cooled to −78° C., was added via cannula. After 10 min 4-bromo-N-methoxy-N-methylbenzamide (0.30 g, 1.2 mmol) in diethylether (2.0 mL), pre-cooled to −78° C., was added. The reaction mixture was kept at −78° C. for 10 min and then allowed to warm up to room temperature and stirred for another hour. HCl (1M, 5 mL) was added and the mixture stirred for 15 min. The phases were separated and the aqueous phase was extracted with ethyl acetate. The combined organic phases were washed with water and brine, dried over MgSO$_4$, and the solvent was evaporated. The crude product was purified by flash column chromatography on silica using methylene chloride as the eluent affording 176 mg (48% yield) of the title compound as a pale yellow solid: mp 47-49° C.; $^1$H NMR (400 MHz, CDCl$_3$) δ 8.55 (br s, 1 H), 8.01 (s, 1 H), 7.87 (m, 2 H), 7.72 (m, 2 H), 7.68 (dd, J=8.2 Hz, J=1.4 Hz, 1 H), 7.52 (m, 1 H), 7.35 (s, 1 H), 6.74 (m, 1 H); $^{13}$C NMR (100.5 MHz, CDCl$_3$) δ 196.5, 138.0, 135.4, 132.0, 131.9, 131.8, 131.4, 128.5, 127.1, 122.4, 120.8, 114.6, 103.6; MS TSP) m/z 300, 302 (M+1).

Method 5

(4-Bromophenyl)(1H-pyrazol4-yl)methanone

The title compound was prepared from 4-bromopyrazole and 4-bromo-N-methoxy-N-methylbenzamide following the general method of Method 1 using two equivalents of t-butyllithium as the base. The crude product was re-crystallized from ethyl acetate and petroleum ether affording 0.28 g (44% yield) of the title compound as colorless crystals: mp 213-215° C.; $^1$H NMR (300 MHz, CD$_3$OD) δ 7.95 (br s, 2 H), 7.58 (m, 2 H), 7.51 (m, 2 H); $^{13}$C NMR (100.5 MHz, CD$_3$OD) δ 190.3, 139.6, 138.8, 133.4, 132.1, 128.6, 123.1; MS (TSP) m/z 251, 253 (M+1).

Method 6

(4-Bromophenyl)(1,3-thiazol-2-yl)methanone

The title compound was prepared from 2-bromothiazole and 4-bromo-N-methoxy-N-methylbenzamide following the general method of Method 1. The crude product was purified by column chromatography on silica gel using petroleum ether/ethyl acetate, 7:3, as the eluent affording 0.52 g (98% yield) of the title compound as a yellow crystals: mp 74-75° C.; $^1$H NMR (400 MHz, CDCl$_3$) δ 8.32 (m, 2 H), 8.02 (d, J=3.0 Hz, 1 H), 7.67 (d, J=3.0 Hz, 1 H), 7.60 (m, 2 H); $^{13}$C NMR (100.5 MHz, CDCl$_3$) δ 183.4, 167.9, 145.3, 134.2, 133.0, 132.2, 129.6, 127.0; MS (TSP) m/z 268, 279 (M+1)

Method 7

3-Acetylmidazo[1,2a]pyridine

Aluminium chloride (20.4 g, 153.2 mmol) was added in small portions to a solution of imidazo[1,2a]pyridine (8.9 g, 75.7 mmol) in dichloromethane (150 mL) cooled at 5° C. The mixture was then allowed to warm to ambient temperature and stirred for 1 hour and then heated to reflux. Acetic anhydride (5.1 mL, 53.9 mmol) was then added slowly over 30 minutes and the mixture heated at reflux for further 90 minutes. The mixture was allowed to cool, the solvent was removed by evaporation and ice/water added to the residue. The aqueous mixture was made alkaline with 2 M aqueous sodium hydroxide solution and extracted with ethyl acetate. The combined extracts were dried and the volatiles removed by evaporation to give a brown oil. This oil was shown to consist of ~35% of the title compound, the remainder being imidazo[1,2,a]pyridine. This mixture was used without further purification; NMR: 2.57 (s, 3 H), 7.22 (dd, 1 H), 7.61 (dd, 1 H), 7.79 (d, 1 H), 8.60 (s, 1 H), 9.52 (d, 1 H).

Method 8

3-(3-Dimethylaminoprop-2-en-1-oyl)imidazo[1,2a]pyridine

A mixture of crude 3-acetylimidazo[1,2,a]pyridine (Method 4; 3.3 g, 19.1 mmol) and DMFDMA (40 mL) was heated at reflux for 60 hours. The mixture was allowed to cool, the volatiles were removed by evaporation and the residue triturated with hot diethyl ether. The solid product was collected by filtration to give the title compound (2.29 g, 52% yield). $^1$H NMR: 2.90 (br s, 3 H), 3.10 (br s, 3 H), 5.81 (d, 1 H), 7.09 (dd, 1H), 7.42 (dd, 1 H), 7.65 (d, 1 H), 7.70 (d, 1 H), 8.43 (s, 1 H), 9.72 (d, 1 H); m/z: 216 [MH]$^+$.

Method 9

2-Amino-4-(imidazo[1,2a]pyrid-3-yl)pyrimidine

A mixture of 3-(3-dimethylaminoprop-2-en-1-oyl)imidazo[1,2a]pyridine (Method 5; 20 g, 0.093 mol), sodium methoxide (20.1 g, 0.372 mol) and guanidine hydrochloride (22.09 g, 0.233 mol) in n-butanol (1500 mL) and methanol (1000 mL) were heated at reflux for 60 hours. The resulting solution was decanted from insoluble material, the volatiles were removed by evaporation and the residue was purified by chromatography eluting with dichloromethane/methanol (97:3) to give the title compound (13 g, 67% yield). NMR: 6.78 (s, 1 H), 7.15-7.05 (m, 2 H), 7.45 (dd, 2 H), 7.70 (d, 1 H), 8.20 (d, 1 H), 8.50 (s, 1 H), 10.15 (d, 1 H); m/z: 212 [MH]$^+$.

Method 10

2-Hydroxy-4-(imidazo[1,2a]pyrid-3-yl)pyrimidine

A solution of sodium nitrate (11.04 g, 0.16 mol) in water (100 mL) was added to a solution of 2-amino-4-(imidazo[1,2a]pyrid-3-yl)pyrimidine (Method 6; 11.27 g, 0.053 mol) in 70% acetic acid (330 mL) at 60° C. The mixture was heated at 60° C. for 3 hours, allowed to cool and neutralised with 5 M aqueous sodium hydroxide solution, the resulting precipitate was collected by filtration, washed quickly with cold water and dried in vacuum oven at 50° C. to give the title compound (9.95 g, 89% yield). NMR: 6.98 (d, 1 H), 7.12 (dd, 1 H), 7.55 (dd, 1 H), 7.80 (d, 1 H), 7.82 (d, 1 H), 8.70 (s, 1 H); m/z: 213 [MH]$^+$.

Method 11

2-Chloro-4-(imidazo[1,2a]pyrid-3-yl)pyrimidine

A suspension of 2-hydroxy4-(imidazo[1,2a]pyrid-3-yl)pyrimidine (Method 7; 9.92 g, 46%) in phosphoryl chloride (200 mL) and phosphorus pentachloride (11 g, 53%) was heated at reflux under nitrogen for 24 hours. Excess phosphoryl chloride was removed by evaporation, ice water was added and the mixture neutralised with 2 M aqueous sodium hydroxide solution. The aqueous mixture was extracted with ethyl acetate, dried and evaporated to give the title compound (7.42 g, 69% yield). NMR: 7.15 (dd, 1 H), 7.59 (dd, 1 H), 7.80 (d, 1 H), 8.05 (d, 1 H), 8.64 (d, 1 H), 8.79 (s, 1 H), 9.72 (d, 1 H(, 7.59 (dd, [MH ]$^+$.

Method 12

4-(Imidazo[1,2a]pyrid-3-yl)-2-methylthiopyrimidine

A mixture of 3-(3-dimethylaminoprop-2-en-1-oyl)imidazo[1,2a]pyridine (Method 5; 0.90 g, 4.2 mmol), thiourea (0.32 g, 4.2 mmol) and sodium methoxide (0.34 g, 6.3 mmol) was heated at 85° C. in N-butanol (10 mL) for 2 hours. The mixture was allowed to cool to 30° C., methyl iodide (0.6 mL, 9.6 mmol) was added dropwise and stirring continued for a further 3 hours. The volatiles were removed by evaporation and the residue purified by chromatography, eluting with ethyl acetate/methanol (100:0 increasing in polarity to 97:3) to give the title compound (0.94 g, 93% yield). NMR: 2.61 .(s, 3 H), 7.22 (dd, 1 H), 7.54 (dd, 1 H), 7.72 (d, 1 H), 7.77 (d, 1 H), 8.56 (d, 1 H), 8.66 (s, 1 H), 9.83 (d, 1 H); m/z: 243 [MH]$^+$.

Pharmaceutical Formulations

According to one aspect of the present invention there is provided a pharmaceutical formulation comprising a compound of formula I, as a free base or a pharmaceutically acceptable salt thereof, for use in the treatment and/or prophylaxis of conditions associated with glycogen synthase kinase-3.

The composition may be in a form suitable for oral administration, for example as a tablet, pill, syrup, powder, granule or capsule, for parenteral injection (including intravenous, subcutaneous, intramuscular, intravascular or infusion) as a sterile solution, suspension or emulsion, for topical administration as an ointment, patch or cream or for rectal administration as a suppository.

In general the above compositions may be prepared in a conventional manner using conventional excipients, pharmaceutical diluents or inert carriers.

Suitable daily doses of the compounds of formula I in the treatment of a mammal, including man are approximately 0.01 to 250 mg/kg bodyweight at peroral administration and about 0.001 to 250 mg/kg bodyweight at parenteral administration. The typical daily dose of the active ingredients varies within a wide range and will depend on various factors such as the relevant indication; the route of administration, the age, weight and sex of the patient and may be determined by a physician.

The following illustrate representative pharmaceutical dosage forms containing a compound of formula I, as a free base or a pharmaceutically acceptable salt thereof (hereafter compound X), for therapeutic and/or prophylactic use in mammals:

| (a): Tablet | Mg/tablet |
|---|---|
| Compound X | 100 |
| Lactose Ph.Eur | 182.75 |
| Croscarmellose sodium | 12.0 |
| Maize starch paste (5% w/v paste) | 2.25 |
| Magnesium stearate | 3.0 |

| (b): Capsule | Mg/capsule |
|---|---|
| Compound X | 10 |
| Lactose Ph.Eur | 488.5 |
| Magnesium stearate | 1.5 |

| (c): Injection | (50 mg/ml) |
|---|---|
| Compound X | 5.0% w/v |
| 1 M Sodium hydroxide solution | 15.0% v/v |
| 0.1 M Hydrochloric acid | (to adjust pH to 7.6) |
| Polyethylene glycol 400 | 4.5% w/v |
| Water for injection | To 100% |

The above formulations may be obtained by conventional procedures well known in the pharmaceutical art.

Medical Use

Surprisingly, it has been found that the compounds defined in the present invention, as a free base or a pharmaceutically acceptable salt thereof are well suited for inhibiting glycogen synthase kinase-3 (GSK3). Accordingly, the compounds of the present invention are expected to be useful in the treatment and/or prophylaxis of conditions associated with glycogen synthase kinase-3 activity, i.e. the compounds may be used to produce an inhibitory effect of GSK3 in mammals, including man in need of such treatment and/or prophylaxis.

GSK3 is highly expressed in the central and peripheral nervous system and in other tissues. Thus, it is expected that a compound of the invention is well suited for the treatment and/or prophylaxis of conditions associated with glycogen synthase kinase-3 in the central and peripheral nervous system. In particular, such compounds of the invention are expected to be suitable for treatment and/or prophylaxis of conditions associated with, especially, dementia, Alzheimer's Disease, Parkinson's Disease, Frontotemporal dementia Parkinson's Type, Parkinson dementia complex of Guam, HIV dementia, diseases with associated neurofibrillar tangle pathologies, amyotrophic lateral sclerosis, corticobasal degeneration, dementia pugilistica, Down's Syndrome, Huntington's Disease, postencephalitic Parkinsonism, progressive supranuclear palsy, Pick's Disease, Niemann-Pick's Disease, Pick's Disease, stroke, head trauma and other chronic neurodegenerative diseases, Bipolar Disease, affective disorders, depression, schizophrenia, cognitive disorders, Type I and Type II diabetes and diabetic neuropathy, hair loss and a condition requiring contraceptive medication.

The dose required for the therapeutic or prophylactic treatment of a particular disease will necessarily be varied depending on the host treated, the route of administration and the severity of the illness being treated.

The present invention relates also to the use of a compound of formula I as defined hereinbefore, in the manufacture of a medicament for the prophylaxis and/or treatment of conditions associated with glycogen synthase kinase-3.

In the context of the present specification, the term "therapy" includes treatment as well as "prophylaxis" unless there are specific indications to the contrary. The terms "therapeutic" and "therapeutically" should be construed accordingly.

The invention also provides a method of treatment and/or prophylaxis of conditions associated with glycogen synthase kinase-3, in a patient suffering from, or at risk of, said condition, which comprises administering to the patient a therapeutically effective amount of a compound of formula I, as hereinbefore defined.

Non-Medical Use

In addition to their use in therapeutic medicine, the compounds of formula I as a free base or a pharmaceutically acceptable salt thereof are also useful as pharmacological tools in the development and standardisation of in vitro and in vivo test systems for the evaluation of the effects of inhibitors of GSK3 related activity in laboratory animals such as cats, dogs, rabbits, monkeys, rats and mice, as part of the search for new therapeutical agents.

Pharmacology

Determination of ATP Competition in Scintillation Proximity GSK3β Assay

GSK3β Scintillation Proximity Assay

The competition experiments were carried out in duplicate with 10 different concentrations of the inhibitors in clear-bottom microtiter plates (Wallac, Finland). A biotinylated peptide substrate, Biotin-Ala-Ala-Glu-Glu-Leu-Asp-Ser-Arg-Ala-Gly-Ser($PO_3H_2$)-Pro-Gln-Leu (AstraZeneca, Lund), was added at a final concentration of 1 µM in an assay buffer containing 1 mU recombinant human GSK3β (Dundee University, UK), 12 mM morpholinepropanesulfonic acid (MOPS), pH 7.0, 0.3 mM EDTA, 0.01% β-mercaptoethanol, 0.004% Brij 35 (a natural detergent), 0.5% glycerol and 0.5 µg BSA/25 µl. The reaction was initiated by the addition of 0.04 µCi [$\gamma$-$^{33}$P]ATP (Amersham, UK) and unlabelled ATP at a final concentration of 1 µM and assay volume of 25 µl. After incubation for 20 minutes at room temperature, each reaction was terminated by the addition of 25 µl stop solution containing 5 mM EDTA, 50 µM ATP, 0.1% Triton X-100 and 0.25 mg streptavidin coated Scintillation Proximity Assay (SPA) beads (Amersham, UK). After 6 hours the radioactivity was determined in a liquid scintillation counter (1450 MicroBeta Trilux, Wallac). The inhibition curves were analysed by non-linear regression using GraphPad Prism, USA. The $K_m$ value of ATP for GSK3β, used to calculate the inhibition constants ($K_i$) of the various compounds, was 20 µM.

The following abbreviations have been used:

| | |
|---|---|
| MOPS | Morpholinepropanesulfonic acid |
| EDTA | Ethylenediaminetetraacetic acid |
| BSA | Bovine Serum Albumin |
| ATP | Adenosine Triphosphate |
| SPA | Scintillation Proximity Assay |
| GSK3 | Glycogen synthase kinase 3 |

Results

Typical $K_i$ values for the compounds of the present invention are in the range of about 0.001 to about 10,000 nM, preferably about 0.001 to about 1000 nM, particularly preferred about 0.001 nM to about 500 nM.

The invention claimed is:
1. A compound having the formula I

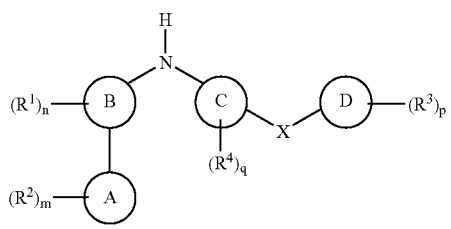

(I)

as a free base or a pharmaceutically acceptable salt thereof wherein:

X is CO;
Ring A is imidazo[1,2a]pyrid-3-yl;
Ring B is pyridine or pyrimidine;
Ring C is a phenyl ring;
Ring D is a phenyl ring, optionally fused with a 5- or 6-membered saturated, partially saturated or unsaturated ring optionally containing atoms selected from C, N, O and S and wherein if said heterocyclic group contains an —NH— moiety that nitrogen may be optionally substituted by a group Q;
$R^1$ is hydrogen, halo, nitro, cyano, hydroxy, fluormethyl, difluoromethyl, trifluoromethyl, fluoromethoxy, difluoromethoxy, trifluoromethoxy, $NH_2$, NHOH, NHCN, $(CO)C_{1-3}$alkyl, $CH=NOR^7$, $(C=NH)NR^7R^8$, $CONH_2$, SH, $SC_{1-3}$alkyl, $SO_2NH_2$, $SONH_2$, $C_{1-3}$alkyl, $C_{3-6}$cycloalkyl, $C_{2-3}$alkenyl, $C_{2-3}$alkynyl, $C_{1-3}$alkoxy, $O(CO)C_{1-3}$alkyl, $NHC_{1-3}$alkyl, $N(C_{1-2}$alkyl$)_2$, $NH(CO)$ $C_{1-3}$alkyl, $CONHC_{1-3}$alkyl, $CON(C_{1-3}$alkyl$)_2$, $SOC_{1-3}$ alkyl, $SO_2C_{1-3}$alkyl, $SO_2NH(C_{1-3}$alkyl), $SO_2N(C_{1-3}$ alkyl$)_2$, $SONHC_{1-3}$alkyl or $SON(C_{1-3}$alkyl$)_2$, wherein any $C_{1-2}$alkyl, $C_{1-3}$alkyl, $C_{2-3}$alkenyl or $C_{2-3}$alkynyl may be optionally substituted on any carbon atoms by one or more J;
n is 1, 2 or 3, wherein each $R^1$ above may be the same or different;
$R^2$, $R^3$ and $R^4$ are attached to a ring carbon and are independently selected from hydrogen, halo, nitro, CHO, $C_{0-6}$alkylCN, $OC_{1-6}$alkylCN, $C_{0-6}$alkyl$OR^7$, $OC_{1-6}$alkyl$OR^7$, fluoromethyl, difluoromethyl, trifluoromethyl, fluoromethoxy, difluoromethoxy, trifluoromethoxy, $C_{0-6}$alkyl$NR^7R^8$, $OC_{1-6}$alkyl$NR^7R^8$, $OC_{1-6}$ alkyl$OC_{1-6}$alkyl$NR^7R^8$, NHOH, $NR^7OR^8$, NHCN, $(CO)C_{1-3}$alkyl, $CH=NOR^7$, $(C=NH)NR^7R^8$, $C_{0-6}$alkyl$CO_2R^7$, $OC_{1-6}$alkyl$CO_2R^7$, $C_{0-6}$alkyl$CONR^7R^8$, $OC_{1-6}$alkyl$CONR^7R^8C_{0-6}$alkyl $NR^7(CO)R^7$, $O(CO)NR^7R^8$, $NR^9(CO)OR^7$, $NR^7(CO)$ $NR^7R^8$, $O(CO)OR^7R^8$, $O(CO)R^7$, $C_{0-6}$alkyl$COR^7$, $OC_{1-6}$alkyl$COR^7$, $OC_{1-6}$alkyl$COR^7$, $NR^7(CO)(CO)R^7$, $NR^7(CO)(CO)NR^7R^8$, $SR^7$, $C_{0-6}$alkyl$(SO_2)NR^7R^8$, $OC_{1-6}$alkyl$NR^7(SO_2)R^8$, $OC_{1-6}$alkyl$(SO_2)NR^7R^8$, $CO_{0-6}$alkyl$(SO)NR^7R^8$, $OC_{1-6}$alkyl$(SO)NR^7R^8$, $SO_3R^7$, $C_{0-6}$alkyl$NR^7(SO_2)NR^7R^8$, $C_{0-6}$alkyl$NR^7(SO)$ $R^8$, $C_{0-6}$alkyl$SO_2R^7$, $C_{0-6}$alkyl$SOR^7$, $C_{1-6}$alkyl, $C_{2-6}$alkenyl, $C_{2-6}$alkynyl, $C_{0-6}$alkyl$C_{3-6}$cycloalkyl, $C_{0-6}$alkylaryl and $C_{0-6}$alkylheterocyclic group, wherein any $C_{1-6}$alkyl, $C_{2-6}$alkenyl, $C_{2-6}$alkynyl, $C_{0-6}$alkyl$C_{3-6}$ cycloalkyl, $C_{0-6}$alkylaryl or $C_{0-6}$alkylheterocyclic group may be optionally substituted on any carbon atom by one or more G; and wherein if said heterocyclic group contains an —NH— moiety, that nitrogen may be optionally substituted by a group Q;
m, p and q is 1, 2, 3, 4 or 5; wherein the definitions of $R^2$, $R^3$ and $R^4$ above may be the same or different;
$R^5$ is hydrogen, fluoromethyl, difluoromethyl, trifluoromethyl, $C_{1-6}$alkyl, $C_{2-6}$alkenyl, $C_{2-6}$alkynyl, $C_{0-6}$alkyl$C_{3-6}$cycloalkyl, $(CO)C_{1-6}$alkyl or $C_{1-6}$alkyl$NR^7R^8$,
$R^6$ is hydrogen, $C_{1-6}$alkyl, $C_{2-6}$alkenyl, $C_{2-6}$alkynyl or trifluoromethyl;
$R^7$ and $R^8$ are independently selected from hydrogen, $C_{1-6}$alkyl, $C_{0-6}$alkyl$C_{3-6}$cycloalkyl, $C_{2-6}$alkenyl, $C_{2-6}$alkynyl, $C_{0-6}$alkylaryl or $C_{0-6}$alkylheterocyclic group; wherein any $C_{1-6}$alkyl, $C_{2-6}$alkenyl, $C_{2-6}$alkynyl and $C_{0-6}$alkyl$C_{3-6}$cycloalkyl, aromatic group or heterocyclic group may be optionally substituted on carbon by one or more G and wherein $R^7$ and $R^8$ together may form a 5- or 6-membered heterocyclic group containing heteroatoms selected from N, O and S, wherein if said heterocyclic group contains an —NH— moiety that nitrogen may be optionally substituted by a group Q;
G and J are independently selected from hydrogen, halo, nitro, cyano, CHO, $OR^9$, $C_{1-6}$alkyl, $C_{2-6}$alkenyl, $C_{2-6}$alkynyl, $C_{0-6}$alkyl$C_{3-6}$cycloalkyl, fluoromethyl, difluoromethyl, trifluoromethyl, fluoromethoxy, difluoromethoxy, trifluoromethoxy, $NR^9R^{10}$, $CO_2R^9$, $CONR^9R^{10}$, $NR^9(CO)R^9$, $O(CO)R^9$, $COR^9$, $SR^9$, $(SO_2)$ $NR^9R^{10}$, $(SO)NR^9R^{10}$, $SO_3R^9$, $SO_2R^9$, $SOR^9$;
$R^9$ and $R^{10}$ are independently selected from hydrogen and $C_{1-6}$alkyl and wherein $R^9$ and $R^{10}$ together may form a 5- or 6-membered heterocyclic group containing heteroatoms selected from N, O and S wherein if said heterocyclic group contains an —NH— moiety that nitrogen may be optionally substituted by a group Q;
Q is selected from $C_{1-4}$alkyl, $COC_{1-4}$alkyl, $SO_2C_{1-4}$alkyl, $(CO)OC)_{1-4}$alkyl, $CONH_2$, $CONHC_{1-4}$alkyl, $CON$ $(C_{1-4}$alkyl$)_2$, benzyl and benzyloxycarbonyl.

2. The compound according to claim 1 wherein Ring B is pyrimidine.

3. A compound which is
2-[4-(4-Morpholinobenzoyl)anilino]-4-(imidazo-[1,2-a]-pyridin-3-yl)pyrimidine,
2-[4-(4-N,N-diethylcarbamoylbenzoyl)anilino]-4-(imidazo-[1,2-a]-pyridin-3-yl)pyrimidine,
2-[4-(4-Methylbenzoyl)anilino]-4-(imidazo-[1,2-a]-pyridin-3-yl)pyrimidine,
2-[4-(4-Cyanobenzoyl)anilino]-4-(imidazo-[1,2-a]-pyridin-3-yl)pyrimidine,
2-[4-(3-Chlorobenzoyl)anilino]-4-(imidazo-[1,2-a]-pyridin-3-yl)pyrimidine,
2-[4-(3-Ethoxybenzoyl)anilino]-4-(imidazo-[1,2-a]-pyridin-3-yl)pyrimidine, 2-(4-benzoylanilino)-4-(imidazo-[1,2-a]-pyridin-3-yl)pyrimidine, (±)-2-[4-(Hydroxyphenylmethyl)anilino]-4-(imidazo-[1,2-a]-pyridin-3-yl)pyrimidine, 2-[4-(1-oxo-2-phenylethyl)anilino]-4-(imidazo-[1,2-a]-pyridin-3-yl)pyrimidine, 2-(3-benzoylanilino)-4-(imidazo-[1,2-a]-pyridin-3-yl)pyrimidine, 2-[4-(1H-indol-6-ylcarbonyl)anilino]-4-(imidazo-[1,2-a]-pyridin-3-yl)pyrimidine, 2-[4-(4,5-dihydro-1H-pyrazol-4-ylcarbonyl)anilino]-4-(imidazo-[1,2-a]-pyridin-3-yl)pyrimidine, or 2-[4-(1,3-thiazol-2-ylcarbonyl)anilino]-4-(imidazo-[1,2-a]-pyridin-3-yl)pyrimidine;

as a free base or a pharmaceutically acceptable salt thereof.

4. A pharmaceutical formulation comprising as active ingredient a therapeutically effective amount of the compound of claim 1 in association with pharmaceutically acceptable diluents, excipients or inert carriers.

5. A process for the preparation of a compound of formula I according to claim 1, wherein $R^1$, $R^2$, $R^3$, $R^4$, X, Ring A, Ring C, Ring D, m, p, q and n are, unless otherwise specified, as defined in formula I and Ring B is pyrimidine or pyridine wherein P is N or $CR^1$, comprising:

a) reacting a pyrimidine or a pyridine of formula II:

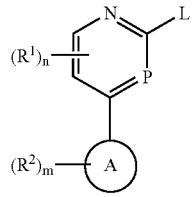

(II)

wherein Ring A, $R^1$, $R^2$, m and n are as defined in formula I, P is N or $CR^1$ and L is an amine or a leaving group;

with a compound of formula III

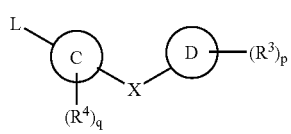

(III)

wherein X, Ring C, Ring D, $R^1$, $R^3$, $R^4$, p and q are as defined in formula I and L is an amine, or a leaving group; one of the L is an amine and the other L is a leaving group, or b) reacting a pyrimidine or a pyridine of formula IV:

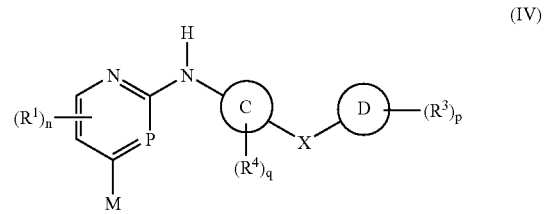

(IV)

wherein X, Ring C, Ring D, $R^3$, $R^4$, p and q are as defined in formula I, P is N or $CR^1$ and M is a leaving group E or a metallic group Y,
with a compound of the formula V:

(V)

wherein Ring A, $R^2$ and m are as defined in formula I, $Q^2$ is a leaving group E or a metallic group Y, one of M or $Q^2$ is a leaving group E and then the other is a metallic group Y; or c) reacting a compound of formula VI:

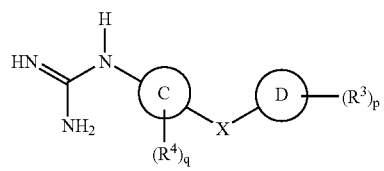

(VI)

wherein X, Ring C, Ring D, $R^3$, $R^4$, p and q are as defined in formula I, with a compound of formula VII:

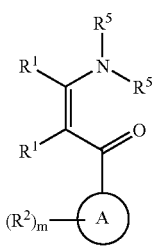

(VII)

wherein Ring A, $R^1$, $R^2$ and m are as defined in formula I and $R^5$ is $C_{1-6}$alkyl, to obtain a compound of formula I, wherein P is N;

and thereafter, if necessary, by conventional methods
i) converting a compound of the formula I into another compound of the formula I, and/or
ii) forming a free base or a pharmaceutically acceptable salt thereof.

* * * * *